(12) United States Patent
Coombs et al.

(10) Patent No.: US 9,538,677 B2
(45) Date of Patent: Jan. 3, 2017

(54) SYSTEM FOR MOBILE DEVICE CRADLE AND TUBE GRIPPER OF NON-DESTRUCTIVE TESTING INSPECTION DEVICE

(71) Applicant: General Electric Company, Schenectady, NY (US)

(72) Inventors: Kevin Andrew Coombs, Onondaga, NY (US); Joshua Lynn Scott, Jordan, NY (US); Gerard Frederick Beckhusen, Baldwinsville, NY (US)

(73) Assignee: General Electric Company, Schenectady, NY (US)

( * ) Notice: Subject to any disclaimer, the term of this patent is extended or adjusted under 35 U.S.C. 154(b) by 585 days.

(21) Appl. No.: 13/800,015

(22) Filed: Mar. 13, 2013

(65) Prior Publication Data
US 2014/0268541 A1    Sep. 18, 2014

(51) Int. Cl.
| | |
|---|---|
| *G02B 23/24* | (2006.01) |
| *H05K 7/00* | (2006.01) |
| *A61B 1/00* | (2006.01) |
| *F01D 21/00* | (2006.01) |

(52) U.S. Cl.
CPC ............. *H05K 7/00* (2013.01); *A61B 1/00039* (2013.01); *A61B 1/00052* (2013.01); *A61B 1/00066* (2013.01); *A61B 1/00105* (2013.01); *F01D 21/003* (2013.01)

(58) Field of Classification Search
CPC . G02B 23/24; G02B 23/2476; A61B 1/00039; A61B 1/00052; A61B 1/00066; A61B 1/00105
USPC .................................................. 600/101-183
See application file for complete search history.

(56) References Cited

U.S. PATENT DOCUMENTS

| | | |
|---|---|---|
| 6,317,039 B1 | 11/2001 | Thomason |
| 6,830,545 B2 | 12/2004 | Bendall |
| 8,059,882 B2 | 11/2011 | Amidi |
| 8,108,168 B2 | 1/2012 | Sharp et al. |
| 8,255,170 B2 | 8/2012 | Kollgaard et al. |
| 2002/0198997 A1 | 12/2002 | Linthicum et al. |
| 2003/0212308 A1 | 11/2003 | Bendall |
| 2010/0145146 A1* | 6/2010 | Melder .................... 600/112 |
| 2011/0112361 A1 | 5/2011 | Ishigami et al. |
| 2011/0130627 A1 | 6/2011 | McGrail et al. |

FOREIGN PATENT DOCUMENTS

EP         1982637 A1    10/2008

OTHER PUBLICATIONS

U.S. Appl. No. 13/747,435, filed Jan. 22, 2013, Jason Howard Messinger.
U.S. Appl. No. 13/747,438, filed Jan. 22, 2013, Jason Howard Messinger.

(Continued)

*Primary Examiner* — Ramon M Barrera
(74) *Attorney, Agent, or Firm* — Fletcher Yoder P.C.

(57) ABSTRACT

A system includes a mobile handset with a handle portion and a gripper portion coupled to the handle portion. The handle portion includes a first dock configured to removably receive a user interface device. The gripper portion is configured to receive an insertion tube of a non-destructive testing (NDT) inspection device and to control the insertion tube relative to an inspection point.

20 Claims, 16 Drawing Sheets

(56) References Cited

OTHER PUBLICATIONS

U.S. Appl. No. 13/747,457, filed Jan. 22, 2013, Jason Howard Messinger.
U.S. Appl. No. 13/747,453, filed Jan. 22, 2013, Sekhar Soorianarayanan.
U.S. Appl. No. 13/747,429, filed Jan. 22, 2013, Sekhar Soorianarayanan.
U.S. Appl. No. 13/747,464, filed Jan. 22, 2013, Sekhar Soorianarayanan.
U.S. Appl. No. 13/747,443, filed Jan. 22, 2013, Jason Howard Messinger.
U.S. Appl. No. 13/747,449, filed Jan. 22, 2013, Michael Christopher Domke.
U.S. Appl. No. 13/747,456, filed Jan. 22, 2013, Michael Christopher Domke.
U.S. Appl. No. 13/747,416, filed Jan. 22, 2013, Michael Christopher Domke.
U.S. Appl. No. 13/747,408, filed Jan. 22, 2013, Michael Christopher Domke.
U.S. Appl. No. 13/732,238, filed Dec. 31, 2012, Michael Christopher Domke.
U.S. Appl. No. 13/732,252, filed Dec. 31, 2012, Kevin Andrew Coombs.
U.S. Appl. No. 13/732,261, filed Dec. 31, 2012, Eugene Schiefer.
U.S. Appl. No. 13/732,281, filed Dec. 31, 2012, Jason Howard Messinger.
U.S. Appl. No. 13/732,293, filed Dec. 31, 2012, Jason Howard Messinger.
U.S. Appl. No. 13/732,303, filed Dec. 31, 2012, Thomas Eldred Lambdin.
U.S. Appl. No. 13/732,268, filed Dec. 31, 2012, Scott Leo Sbihli.
U.S. Appl. No. 13/732,309, filed Dec. 31, 2012, Jason Howard Messinger.
U.S. Appl. No. 13/732,272, filed Dec. 31, 2012, Jason Howard Messinger.
U.S. Appl. No. 13/732,319, filed Dec. 31, 2012, Kevin Andrew Coombs.
U.S. Appl. No. 13/732,327, filed Dec. 31, 2012, Kevin Andrew Coombs.
EP Search Report and Written Opinion issued May 22, 2014 in connection with corresponding EP Patent Application No. 14157927.6.
Sorrel, Charlie. iControlPad Ships at Last [online], [retrieved on Mar. 21, 2013]. Retrieved from the Internet <URL: http://www.wired.com/gadgetlab/2011/11/icontrolpad-ships-at-last/>.
OmniScan MX [online]. Page 5. Olympus, 2010 [retrieved on Mar. 28, 2013]. Retrieved from the Internet: <URL: www.olympus-ims.com/en/omniscan-mx/>.
Georgeson, Gary. [online], [retrieved on Mar. 28, 2013]. http://www.meetingdata.utcdayton.com/agenda/airworthiness/2012/proceedings/presentations/P5526.pdf.
Phasor XS User's Manual [online]. General Electric: Measurement & Control Solutions. [retrieved on Mar. 28, 2013]. Retrieved from the Internet: <URL: www.ge-mcs.com/download/ultrasound/portable-flaw-detectors/Phasor%20Series/om-phasor-en_rev10.pdf>.
USM Vision 1.2—A Total Weld Inspection Solution to Increase Productivity in New Process Pipework Fabrication [online]. General Electric: Measurement & Control. [retrieved on Mar. 28, 2013]. Retrieved from the Internet: <URL: www.ge-mcs.com/download/ultrasound/portable-flaw-detectors/usm-vision/GEIT-USMVision-20058EN_LR.pdf>.
Inviz (R) Vuman (R) RA-Y, "Operation Manual," viZaar Industrial Imaging AG, Oct. 2011, 59 pgs.
Iplex FX, "Longer Reach Better Vision," Olympus Corporation, May 2008, 2 pgs.
Iplex YS, "Innovative Extra-long 30 m Scope," Olympus Corporation, Mar. 2013, 3 pgs.

\* cited by examiner

SYSTEM FOR MOBILE DEVICE CRADLE AND TUBE GRIPPER OF NON-DESTRUCTIVE TESTING INSPECTION DEVICE

CROSS-REFERENCE TO RELATED APPLICATIONS

This application is related to U.S. patent application Ser. No. 13/732,261, entitled "SYSTEMS AND METHODS FOR VIRTUAL CONTROL OF A NON-DESTRUCTIVE TESTING SYSTEM", filed Dec. 31, 2012, which is herein incorporated by reference in its entirety. This application is additionally related to U.S. Pat. No. 6,830,545, entitled "TUBE GRIPPER INTEGRAL WITH CONTROLLER FOR ENDOSCOPE OF BORESCOPE", filed May 13, 2002, which is herein incorporated by reference in its entirety.

BACKGROUND

The subject matter disclosed herein relates to non-destructive testing (NDT) system, and particularly to systems and methods for a mobile device cradle and tube gripper of a NDT inspection device.

Certain equipment and facilities, such as power generation equipment and facilities, oil and gas equipment and facilities, aircraft equipment and facilities, manufacturing equipment and facilities, and the like, include a plurality of interrelated systems, and processes. For example, power generation plants may include turbine systems and processes for operating and maintaining the turbine systems. Likewise, oil and gas operations may include carbonaceous fuel retrieval systems and processing equipment interconnected via pipelines. Similarly, aircraft systems may include airplanes and maintenance hangars useful in maintaining airworthiness and providing for maintenance support. During equipment operations, the equipment may degrade, encounter undesired conditions such as corrosion, wear and tear, and so on, potentially affecting overall equipment effectiveness. Certain inspection techniques, such as non-destructive inspection techniques or non-destructive testing (NDT) techniques, may be used to detect undesired equipment conditions.

In a conventional NDT system, an insertion tube with sensors at a head end is used to inspect the equipment and facilities at an inspection point. The sensors at the head end obtain inspection data and transmit the inspection data to an NDT inspection device (e.g., base unit). The head end may be moved via controls on the NDT inspection device. Additionally, sensor data may be processed and monitored by the NDT inspection device. However, the inspection point may be remote from the NDT inspection device. Accordingly, it would be beneficial to control and monitor the head end of the insertion tube near the inspection point.

BRIEF DESCRIPTION

In one embodiment, a system includes a mobile handset with a handle portion and a gripper portion coupled to the handle portion. The handle portion includes a first dock configured to removably receive a user interface device. The gripper portion is configured to receive an insertion tube of a non-destructive testing (NDT) inspection device and to control the insertion tube relative to an inspection point.

In another embodiment, a system includes a mobile handset having a first dock configured to receive a mobile device, and a gripper portion coupled to the first dock. The mobile device is communicatively coupled to a non-destructive testing (NDT) inspection device. The gripper portion is configured to receive an insertion tube of the NDT inspection device. The gripper portion is also configured to control the insertion tube relative to an inspection point.

In yet another embodiment, a system includes a borescope and a mobile handset. The borescope includes a camera configured to transmit image signals along an insertion tube, storage circuitry, and processing circuitry. The storage circuitry is capable of storing one or more executable routines, image signals, or both. The processing circuitry is configured to execute one or more executable routines, to control the camera, to process image signals into image data, and to transmit the image data to a user interface device. The mobile handset is coupled to the insertion tube and includes a handle portion and a gripper portion. The handle portion includes a first dock configured to removably receive the user interface device. The user interface device is configured to communicate with the processing circuitry. The gripper portion is configured to receive the insertion tube and to control the insertion tube relative to an inspection point.

BRIEF DESCRIPTION OF THE DRAWINGS

These and other features, aspects, and advantages of the present invention will become better understood when the following detailed description is read with reference to the accompanying drawings in which like characters represent like parts throughout the drawings, wherein.

DETAILED DESCRIPTION

Figure 1:
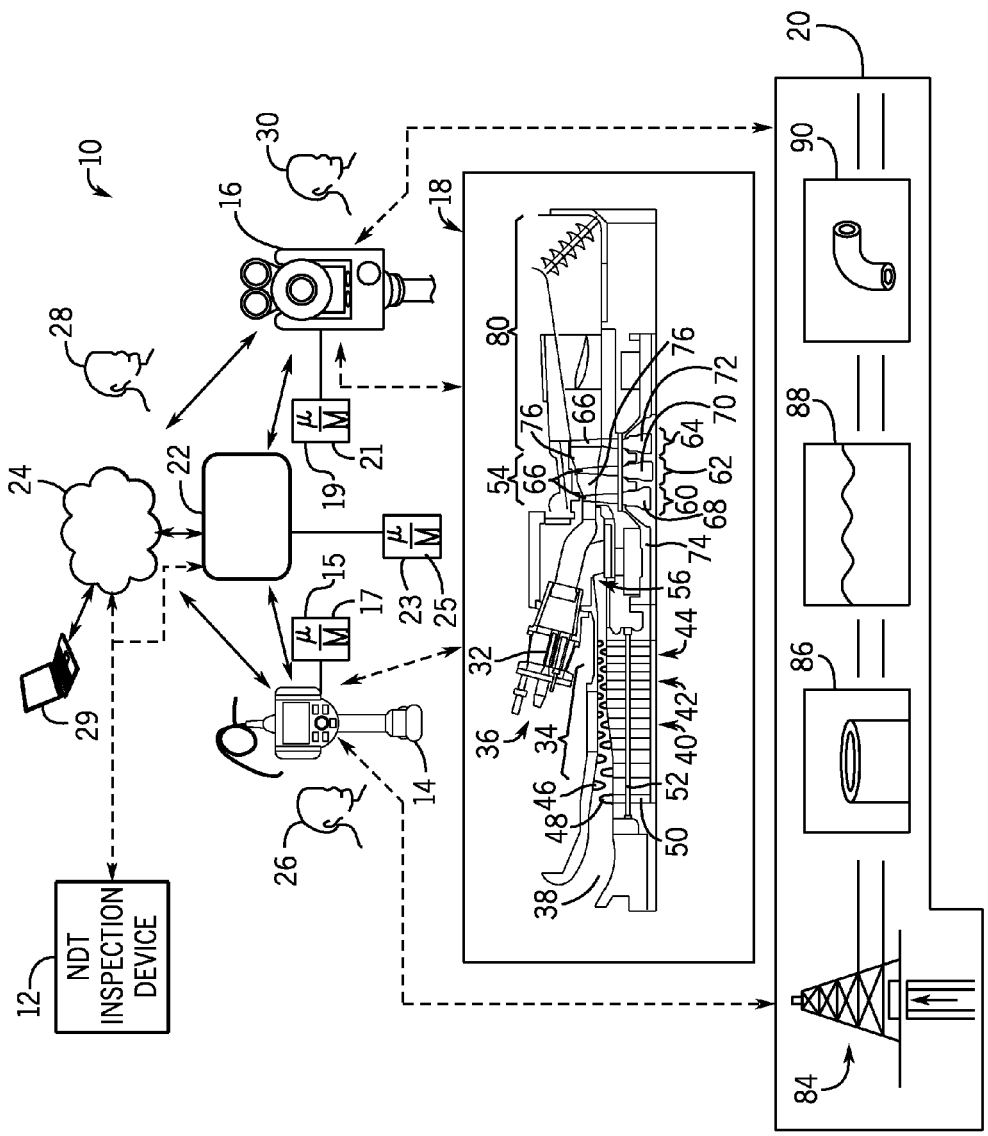
FIG. 1 is a block diagram illustrating an embodiment of a distributed non-destructive testing (NDT) system, including a mobile device.

One or more specific embodiments will be described below. In an effort to provide a concise description of these embodiments, not all features of an actual implementation are described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

When introducing elements of various embodiments of the present invention, the articles "a," "an," "the," and "said" are intended to mean that there are one or more of the elements. The terms "comprising," "including," and "having" are intended to be inclusive and mean that there may be additional elements other than the listed elements.

Embodiments of the present disclosure may apply to a variety of inspection and testing techniques, including non-destructive testing (NDT) or inspection systems. In the NDT system, certain techniques such as borescopic inspection, weld inspection, remote visual inspections, x-ray inspection, ultrasonic inspection, eddy current inspection, and the like, may be used to analyze and detect a variety of conditions, including but not limited to corrosion, equipment wear and tear, cracking, leaks, and so on. The techniques described herein provide for improved NDT systems suitable for borescopic inspection, remote visual inspections, x-ray inspection, ultrasonic inspection, and/or eddy current inspection, enabling enhanced data gathering, data analysis, inspection/testing processes, and NDT collaboration techniques.

The improved NDT systems described herein may include inspection equipment using wireless conduits suitable for communicatively coupling the inspection equipment to mobile devices, such as tablets, smart phones, and augmented reality eyeglasses; to computing devices, such as notebooks, laptops, workstations, personal computers; and to "cloud" computing systems, such as cloud-based NDT ecosystems, cloud analytics, cloud-based collaboration and workflow systems, distributed computing systems, expert systems and/or knowledge-based systems. Indeed, the techniques described herein may provide for enhanced NDT data gathering, analysis, and data distribution, thus improving the detection of undesired conditions, enhancing maintenance activities, and increasing returns on investment (ROI) of facilities and equipment.

In one embodiment, a tablet may be communicatively coupled to the NDT inspection device (e.g., borescope, transportable pan-tilt-zoom camera, eddy current device, x-ray inspection device, ultrasonic inspection device), such as a MENTOR™ NDT inspection device, available from General Electric, Co., of Schenectady, N.Y., and used to provide, for example, enhanced wireless display capabilities, remote control, data analytics and/or data communications to the NDT inspection device. While other mobile devices may be used, the use of the tablet is apt, however, insofar as the tablet may provide for a larger, higher resolution display, more powerful processing cores, an increased memory, and improved battery life. Accordingly, the tablet may address certain issues, such as providing for improved visualization of data, improving the manipulatory control of the inspection device, and extending collaborative sharing to a plurality of external systems and entities.

Keeping the foregoing in mind, the present disclosure is directed towards a mobile handset to hold the mobile device and insertion tube near an inspection point. The mobile handset may be attached to the insertion tube between the head end section (e.g., inspection point) and the NDT inspection device. The mobile handset and/or the mobile device may be used to control the head end section and sensors of the insertion tube. The mobile handset and mobile device may be lighter in weight than the NDT inspection device. The mobile handset may also be adjustable to accommodate mobile devices of various geometries. Portions of the mobile handset may be adjustable to position and orient the attached mobile device as desired relative to the insertion tube. The mobile handset may provide power to the mobile device, communicate with the mobile device, and communicate with the NDT inspection device.

By way of introduction, and turning now to FIG. 1, the figure is a block diagram of an embodiment of distributed NDT system 10. In the depicted embodiment, the distributed NDT system 10 may include one or more NDT inspection devices 12. The NDT inspection devices 12 may be divided into at least two categories. In one category, depicted in FIG. 1, the NDT inspection devices 12 may include devices suitable for visually inspecting a variety of equipment and environments. In another category, described in more detail with respect to FIG. 2 below, the NDT devices 12 may include devices providing for alternatives to visual inspection modalities, such as x-ray inspection modalities, eddy current inspection modalities, and/or ultrasonic inspection modalities.

In the depicted first example category of FIG. 1, the NDT inspection devices 12 may include a borescope 14 having one or more processors 15 and a memory 17, and a transportable pan-tilt-zoom (PTZ) camera 16 having one or more processors 19 and a memory 21. In this first category of visual inspection devices, the bore scope 14 and PTZ camera 16 may be used to inspect, for example, a turbo machinery 18, and a facility or site 20. As illustrated, the bore scope 14 and the PTZ camera 16 may be communicatively coupled to a mobile device 22 also having one or more processors 23 and a memory 25. The mobile device 22 may include, for example, a tablet, a cell phone (e.g., smart phone), a notebook, a laptop, or any other mobile computing device. The use of a tablet, however, is apt insofar as the tablet provides for a good balance between screen size, weight, computing power, and battery life. Accordingly, in one embodiment, the mobile device 22 may be the tablet mentioned above, that provides for touchscreen input. The mobile device 22 may be communicatively coupled to the NDT inspection devices 12, such as the bore scope 14 and/or the PTZ camera 16, through a variety of wireless or wired conduits. For example, the wireless conduits may include WiFi (e.g., Institute of Electrical and Electronics Engineers [IEEE] 802.11x), cellular conduits (e.g., high speed packet access [HSPA], HSPA+, long term evolution [LTE], WiMax), near field communications (NFC), Bluetooth, personal area networks (PANs), and the like. The wireless conduits may use a variety of communication protocols, such as TCP/IP, UDP, SCTP, socket layers, and so on. In certain embodiments, the wireless or wired conduits may include secure layers, such as secure socket layers (SSL), virtual private network (VPN) layers, encrypted layers, challenge key authentication layers, token authentication layers, and so on. Wired conduits may include proprietary cabling, RJ45 cabling, co-axial cables, fiber optic cables, and so on.

Additionally or alternatively, the mobile device 22 may be communicatively coupled to the NDT inspection devices 12, such as the borescope 14 and/or the PTZ camera 16, through the "cloud" 24. Indeed, the mobile device 22 may use the cloud 24 computing and communications techniques (e.g., cloud-computing network), including but not limited to HTTP, HTTPS, TCP/IP, service oriented architecture (SOA) protocols (e.g., simple object access protocol [SOAP], web services description languages (WSDLs)) to interface with the NDT inspection devices 12 from any geographic location, including geographic locations remote from the physical location about to undergo inspection. Further, in one embodiment, the mobile device 22 may provide "hot spot" functionality in which mobile device 22 may provide wireless access point (WAP) functionality suitable for connecting the NDT inspection devices 12 to other systems in the cloud 24, or connected to the cloud 24, such as a computing system 29 (e.g., computer, laptop, virtual machine(s) [VM], desktop, workstation). Accordingly, collaboration may be enhanced by providing for multi-party workflows, data gathering, and data analysis.

For example, a borescope operator 26 may physically manipulate the borescope 14 at one location, while a mobile device operator 28 may use the mobile device 22 to interface with and physically manipulate the bore scope 14 at a second location through remote control techniques. The second location may be proximate to the first location, or geographically distant from the first location. Likewise, a camera operator 30 may physically operate the PTZ camera 16 at a third location, and the mobile device operator 28 may remote control PTZ camera 16 at a fourth location by using the mobile device 22. The fourth location may be proximate to the third location, or geographically distant from the third location. Any and all control actions performed by the operators 26 and 30 may be additionally performed by the operator 28 through the mobile device 22. Additionally, the operator 28 may communicate with the operators 26 and/or 30 by using the devices 14, 16, and 22 through techniques such as voice over IP (VOIP), virtual whiteboarding, text messages, and the like. By providing for remote collaboration techniques between the operator 28 operator 26, and operator 30, the techniques described herein may provide for enhanced workflows and increase resource efficiencies. Indeed, nondestructive testing processes may leverage the communicative coupling of the cloud 24 with the mobile device 22, the NDT inspection devices 12, and external systems coupled to the cloud 24.

In one mode of operation, the mobile device 22 may be operated by the bore scope operator 26 and/or the camera operator 30 to leverage, for example, a larger screen display, more powerful data processing, as well as a variety of interface techniques provided by the mobile device 22, as described in more detail below. Indeed, the mobile device 22 may be operated alongside or in tandem with the devices 14 and 16 by the respective operators 26 and 30. This enhanced flexibility provides for better utilization of resources, including human resources, and improved inspection results.

Whether controlled by the operator 28, 26, and/or 30, the borescope 14 and/or PTZ camera 16 may be used to visually inspect a wide variety of equipment and facilities. For example, the bore scope 14 may be inserted into a plurality of borescope ports and other locations of the turbomachinery 18, to provide for illumination and visual observations of a number of components of the turbomachinery 18. In the depicted embodiment, the turbo machinery 18 is illustrated as a gas turbine suitable for converting carbonaceous fuel into mechanical power. However, other equipment types may be inspected, including compressors, pumps, turbo expanders, wind turbines, hydroturbines, industrial equipment, and/or residential equipment. The turbomachinery 18 (e.g., gas turbine) may include a variety of components that may be inspected by the NDT inspection devices 12 described herein.

With the foregoing in mind, it may be beneficial to discuss certain turbomachinery 18 components that may be inspected by using the embodiments disclosed herein. For example, certain components of the turbomachinery 18 depicted in FIG. 1, may be inspected for corrosion, erosion, cracking, leaks, weld inspection, and so on. Mechanical systems, such as the turbomachinery 18, experience mechanical and thermal stresses during operating conditions, which may require periodic inspection of certain components. During operations of the turbomachinery 18, a fuel such as natural gas or syngas, may be routed to the turbomachinery 18 through one or more fuel nozzles 32 into a combustor 36. Air may enter the turbomachinery 18 through an air intake section 38 and may be compressed by a compressor 34. The compressor 34 may include a series of stages 40, 42, and 44 that compress the air. Each stage may include one or more sets of stationary vanes 46 and blades 48 that rotate to progressively increase the pressure to provide compressed air. The blades 48 may be attached to rotating wheels 50 connected to a shaft 52. The compressed discharge air from the compressor 34 may exit the compressor 34 through a diffuser section 56 and may be directed into the combustor 36 to mix with the fuel. For example, the fuel nozzles 32 may inject a fuel-air mixture into the combustor 36 in a suitable ratio for optimal combustion, emissions, fuel consumption, and power output. In certain embodiments, the turbomachinery 18 may include multiple combustors 36 disposed in an annular arrangement. Each combustor 36 may direct hot combustion gases into a turbine 54.

As depicted, the turbine 54 includes three separate stages 60, 62, and 64 surrounded by a casing 76. Each stage 60, 62, and 64 includes a set of blades or buckets 66 coupled to a respective rotor wheel 68, 70, and 72, which are attached to a shaft 74. As the hot combustion gases cause rotation of turbine blades 66, the shaft 74 rotates to drive the compressor 34 and any other suitable load, such as an electrical generator. Eventually, the turbomachinery 18 diffuses and exhausts the combustion gases through an exhaust section 80. Turbine components, such as the nozzles 32, intake 38, compressor 34, vanes 46, blades 48, wheels 50, shaft 52, diffuser 56, stages 60, 62, and 64, blades 66, shaft 74, casing 76, and exhaust 80, may use the disclosed embodiments, such as the NDT inspection devices 12, to inspect and maintain said components.

Additionally, or alternatively, the PTZ camera 16 may be disposed at various locations around or inside of the turbo machinery 18, and used to procure visual observations of these locations. The PTZ camera 16 may additionally include one or more lights suitable for illuminating desired locations, and may further include zoom, pan and tilt techniques described in more detail below with respect to FIG. 4, useful for deriving observations around in a variety of difficult to reach areas. The borescope 14 and/or the camera 16 may be additionally used to inspect the facilities 20, such as an oil and gas facility 20. Various equipment such as oil and gas equipment 84, may be inspected visually by using the borescope 14 and/or the PTZ camera 16. Advantageously, locations such as the interior of pipes or conduits 86, underwater (or underfluid) locations 88, and difficult to observe locations such as locations having curves or bends 90, may be visually inspected by using the mobile device 22 through the borescope 14 and/or PTZ camera 16. Accordingly, the mobile device operator 28 may more safely and efficiently inspect the equipment 18, 84 and locations 86, 88, and 90, and share observations in real-time or near real-time with location geographically distant from the inspection areas. It is to be understood that other NDT inspection devices 12 may be use the embodiments described herein, such as fiberscopes (e.g., articulating fiberscope, non-articulating fiberscope), and remotely operated vehicles (ROVs), including robotic pipe inspectors and robotic crawlers.

Figure 2:
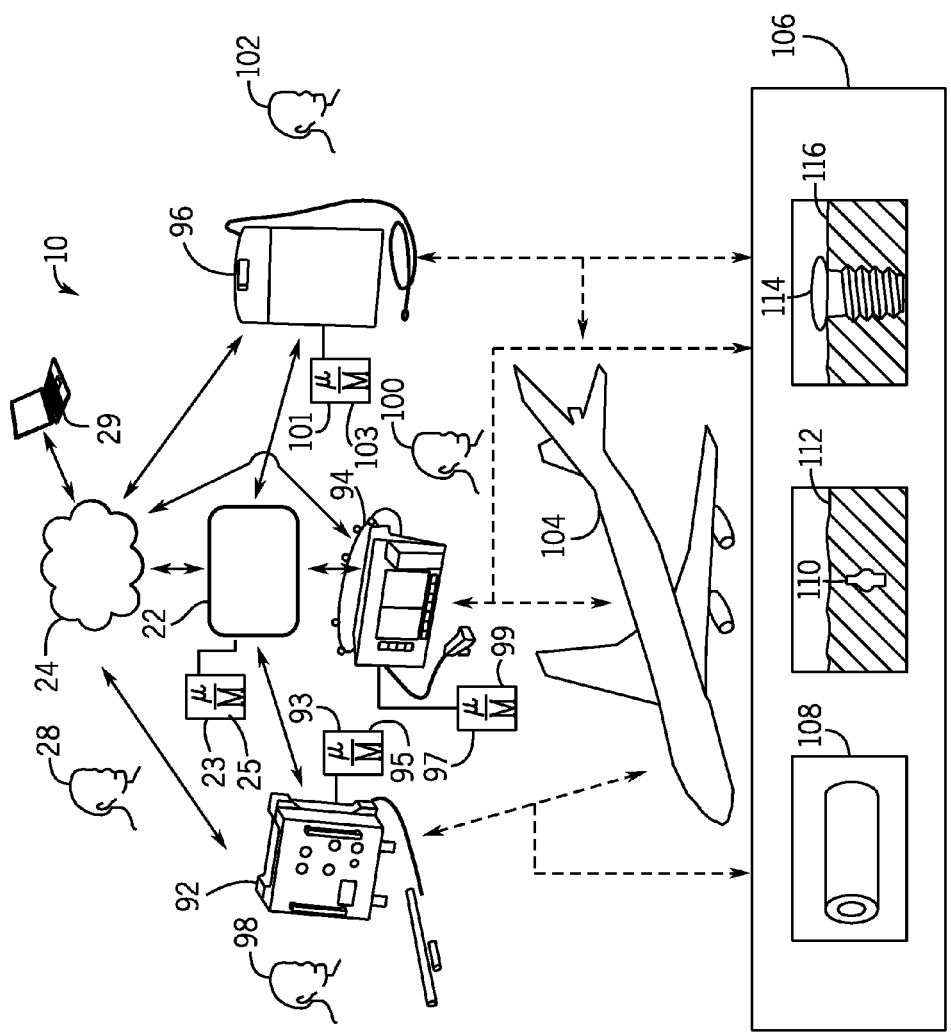
FIG. 2 is a block diagram illustrating further details of an embodiment of the distributed NDT system of FIG. 1.

Turning now to FIG. 2, the figure is a block diagram of an embodiment of the distributed NDT system 10 depicting the second category of NDT inspection devices 12 that may be able to provide for alternative inspection data to visual inspection data. For example, the second category of NDT inspection devices 12 may include an eddy current inspection device 92, an ultrasonic inspection device, such as an ultrasonic flaw detector 94, and an x-ray inspection device, such a digital radiography device 96. The eddy current inspection device 92 may include one or more processors 93 and a memory 95. Likewise, the ultrasonic flaw detector 94 may include one or more processors 97 and a memory 104. Similarly, the digital radiography device 96 may include one or more processors 101 and a memory 103. In operations, the eddy current inspection device 92 may be operated by an eddy current operator 98, the ultrasonic flaw detector 94 may be operated by an ultrasonic device operator 100, and the digital radiography device 96 may be operated by a radiography operator 102.

As depicted, the eddy current inspection device 92, the ultrasonic flaw detector 94, and the digital radiography inspection device 96, may be communicatively coupled to the mobile device 22 by using wired or wireless conduits, including the conduits mentioned above with respect to FIG. 1. Additionally, or alternatively, the devices 92, 94, and 96 may be coupled to the mobile device 22 by using the cloud 24, for example the borescope 14 may be connected to a cellular "hotspot," and use the hotspot to connect to one or more experts in borescopic inspection and analysis. Accordingly, the mobile device operator 28 may remotely control various aspects of operations of the devices 92, 94, and 96 by using the mobile device 22, and may collaborate with the operators 98, 100, and 102 through voice (e.g., voice over IP [VOIP]), data sharing (e.g., whiteboarding), providing data analytics, expert support and the like, as described in more detail herein.

Accordingly, it may be possible to enhance the visual observation of various equipment, such as an aircraft system 104 and facilities 106, with x-ray observation modalities, ultrasonic observation modalities, and/or eddy current observation modalities. For example, the interior and the walls of pipes 108 may be inspected for corrosion and/or erosion. Likewise, obstructions or undesired growth inside of the pipes 108 may be detected by using the devices 92, 94, and/or 96. Similarly, fissures or cracks 110 disposed inside of certain ferrous or non-ferrous material 112 may be observed. Additionally, the disposition and viability of parts 114 inserted inside of a component 116 may be verified. Indeed, by using the techniques described herein, improved inspection of equipment and components 104, 108, 112 and 116 may be provided. For example, the mobile device 22 may be used to interface with and provide remote control of the devices 14, 16, 92, 94, and 96.

Figure 3:
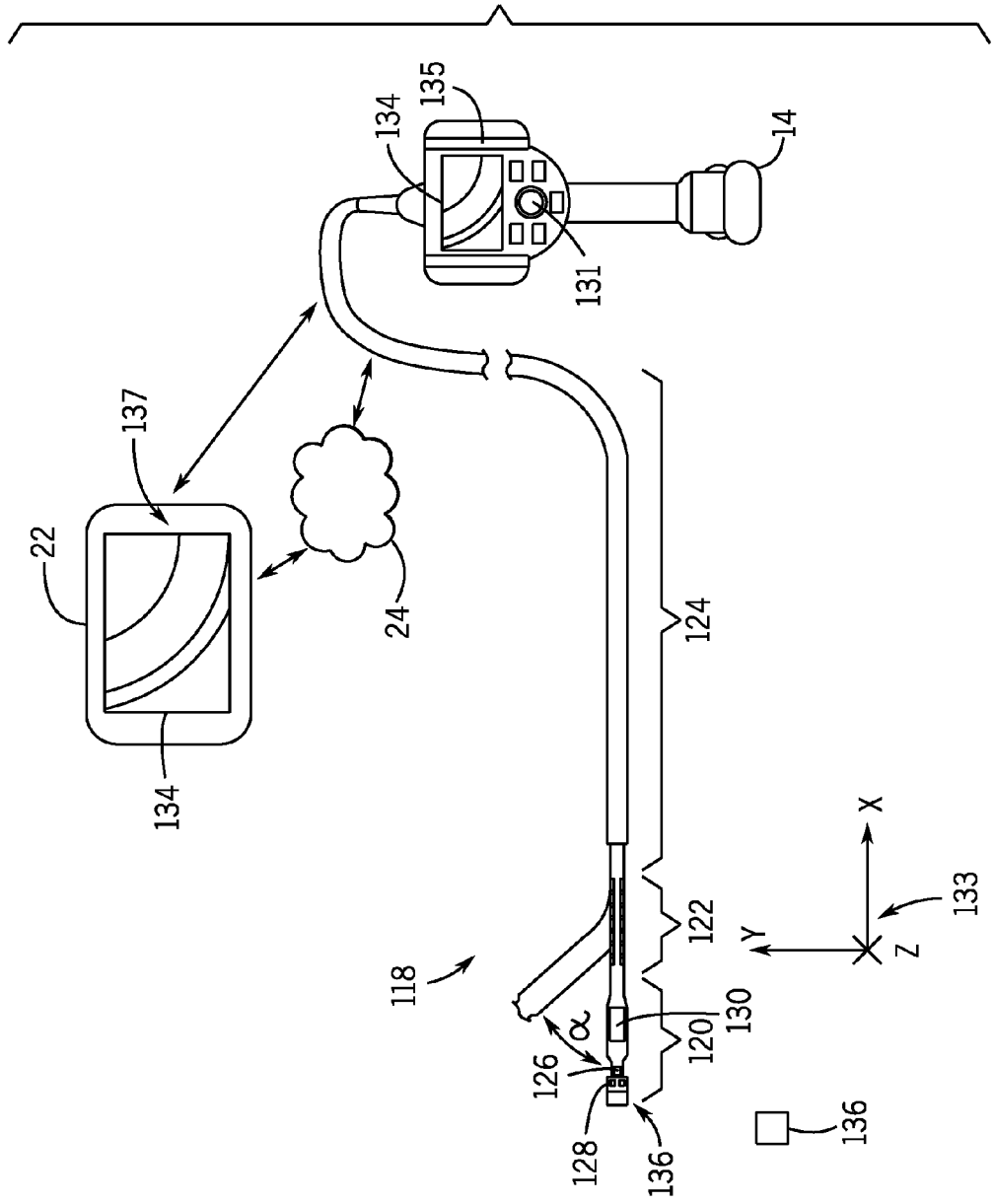
FIG. 3 is a front view illustrating an embodiment of a borescope system 14 communicatively coupled to the mobile device of FIG. 1 and a "cloud;"

FIG. 3 is a front view of the borescope 14 coupled to the mobile device 22 and the cloud 24. Accordingly, the borescope 14 may provide data to any number of devices connected to the cloud 24 or inside the cloud 24. As mentioned above, the mobile device 22 may be used to receive data from the borescope 14, to remote control the borescope 14, or a combination thereof. Indeed, the techniques described herein enable, for example, the communication of a variety of data from the borescope 14 to the mobile device 22, including but not limited to images, video, and sensor measurements, such as temperature, pressure, flow, clearance (e.g., measurement between a stationary component and a rotary component), and distance measurements. Likewise, the mobile device 22 may communicate control instructions, reprogramming instructions, configuration instructions, and the like, as described in more detail below.

As depicted the borescope 14, includes an insertion tube 118 suitable for insertion into a variety of location, such as inside of the turbomachinery 18, equipment 84, pipes or conduits 86, underwater locations 88, curves or bends 90, varies locations inside or outside of the aircraft system 104, the interior of pipe 108, and so on. The insertion tube 118 may include a head end section 120, an articulating section 122, and a conduit section 124. In the depicted embodiment, the head end section 120 may include a camera 126, one or more lights 128 (e.g., LEDs), and sensors 130. As mentioned above, the borescope's camera 126 may provide images and video suitable for inspection. The lights 128 may be used to provide for illumination when the head end 120 is disposed in locations having low light or no light.

During use, the articulating section 122 may be controlled, for example, by the mobile device 22 and/or a physical joy stick 131 disposed on the borescope 14. The articulating sections 122 may steer or "bend" in various dimensions. For example, the articulation section 122 may enable movement of the head end 120 in an X-Y plane X-Z plane and/or Y-Z plane of the depicted XYZ axes 133. Indeed, the physical joystick 131 and/or the mobile device 22 may both be used alone or in combination, to provide control actions suitable for disposing the head end 120 at a variety of angles, such as the depicted angle α. In this manner, the borescope head end 120 may be positioned to visually inspect desired locations. The camera 126 may then capture, for example, a video 134, which may be displayed in a screen 135 of the borescope 14 and a screen 137 of the mobile device 22, and may be recorded by the borescope 14 and/or the mobile device 22. In one embodiment, the screens 135 and 137 may be multi-touchscreens using capacitance techniques, resistive techniques, infrared grid techniques, and the like, to detect the touch of a stylus and/or one or more human fingers. Additionally or alternatively, images and the video 134 may be transmitted into the cloud 24.

Other data, including but not limited to sensor 130 data, may additionally be communicated and/or recorded by the borescope 14. The sensor 130 data may include temperature data, distance data, clearance data (e.g., distance between a rotating and a stationary component), flow data, and so on. In certain embodiments, the borescope 14 may include a plurality of replacement tips 136. For example, the replacement tips 136 may include retrieval tips such as snares, magnetic tips, gripper tips, and the like. The replacement tips 136 may additionally include cleaning and obstruction removal tools, such as wire brushes, wire cutters, and the like. The tips 136 may additionally include tips having differing optical characteristics, such as focal length, stereoscopic views, 3-dimensional (3D) phase views, shadow views, and so on. Additionally or alternatively, the head end 120 may include a removable and replaceable head end 120. Accordingly, a plurality of head ends 120 may be provided at a variety of diameters, and the insertion tube 118 maybe disposed in a number of locations having openings from approximately one millimeter to ten millimeters or more. Indeed, a wide variety of equipment and facilities may be inspected, and the data may be shared through the mobile device 22 and/or the cloud 24.

Figure 4:
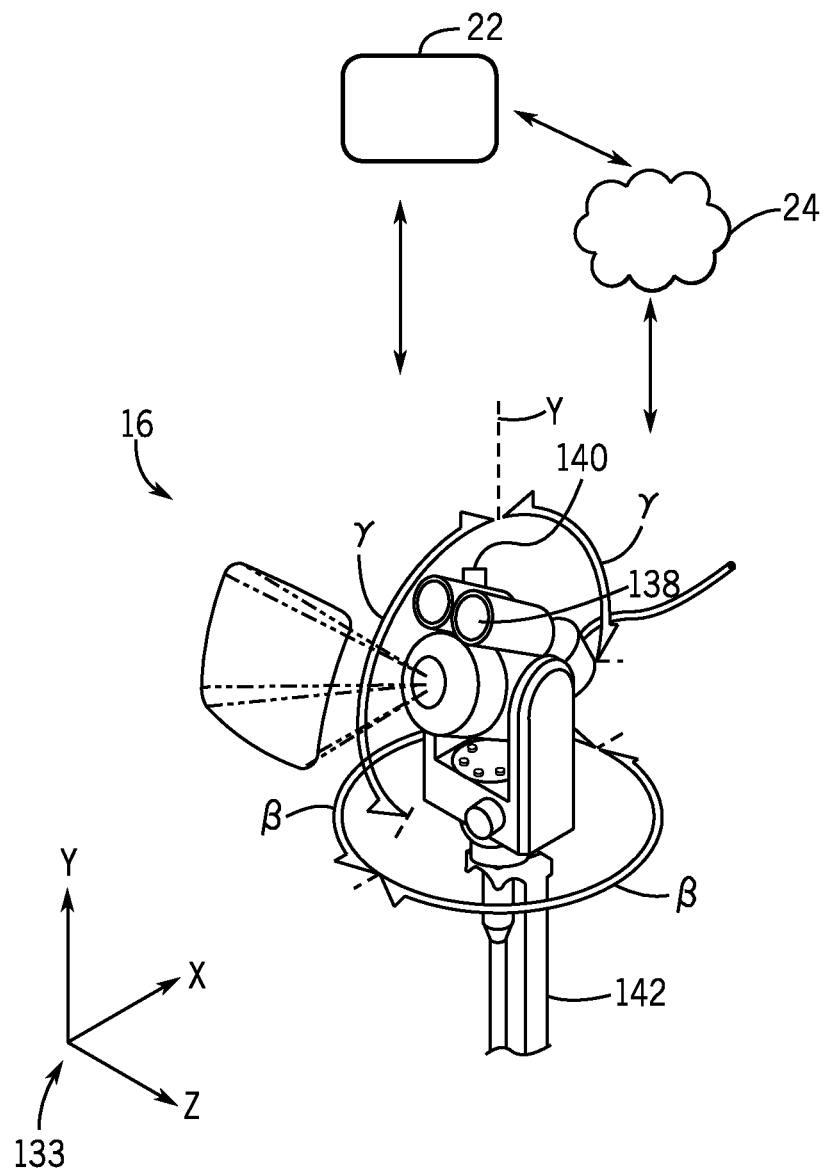
FIG. 4 is an illustration of an embodiment of a pan-tilt-zoom (PTZ) camera system communicatively coupled to the mobile device of FIG. 1.

FIG. 4 is a perspective view of an embodiment of the transportable PTZ camera 16 communicatively coupled to the mobile device 22 and to the cloud 24. As mentioned above, the mobile device 22 and/or the cloud 24 may remotely manipulate the PTZ camera 16 to position the PTZ camera 16 to view desired equipment and locations. In the depicted example, the PTZ camera 16 may be tilted and rotated about the Y-axis. For example, the PTZ camera 16 may be rotated at an angle β between approximately 0° to 180°, 0° to 270°, 0° to 360°, or more about the Y-axis. Likewise, the PTZ camera 16 may be tilted, for example, about the Y-X plane at an angle γ of approximately 0° to 100°, 0° to 120°, 0° to 150°, or more with respect to the Y-Axis. Lights 138 may be similarly controlled, for example, to active or deactivate, and to increase or decrease a level of illumination (e.g., lux) to a desired value. Sensors 140, such as a laser rangefinder, may also be mounted onto the PTZ camera 16, suitable for measuring distance to certain objects. Other sensors 140 may be used, including long-range temperature sensors (e.g., infrared temperature sensors), pressure sensors, flow sensors, clearance sensors, and so on.

The PTZ camera 16 may be transported to a desired location, for example, by using a shaft 142. The shaft 142 enables the camera operator 30 to move the camera and to position the camera, for example, inside of locations 86, 108, underwater 88, into hazardous (e.g., hazmat) locations, and so on. Additionally, the shaft 142 may be used to more permanently secure the PTZ camera 16 by mounting the shaft 142 onto a permanent or semi-permanent mount. In this manner, the PTZ camera 16 may be transported and/or secured at a desired location. The PTZ camera 16 may then transmit, for example by using wireless techniques, image data, video data, sensor 140 data, and the like, to the mobile device 22 and/or cloud 24. Accordingly, data received from the PTZ camera 16 may be remotely analyzed and used to determine the condition and suitability of operations for desired equipment and facilities. Indeed, the techniques described herein may provide for a comprehensive inspection and maintenance process suitable for planning, inspecting, analyzing, and/or sharing a variety of data by using the aforementioned devices 12, 14, 16, 22, 92, 94, 96, and the cloud 24, as described in more detail below with respect to FIG. 5.

Figure 5:
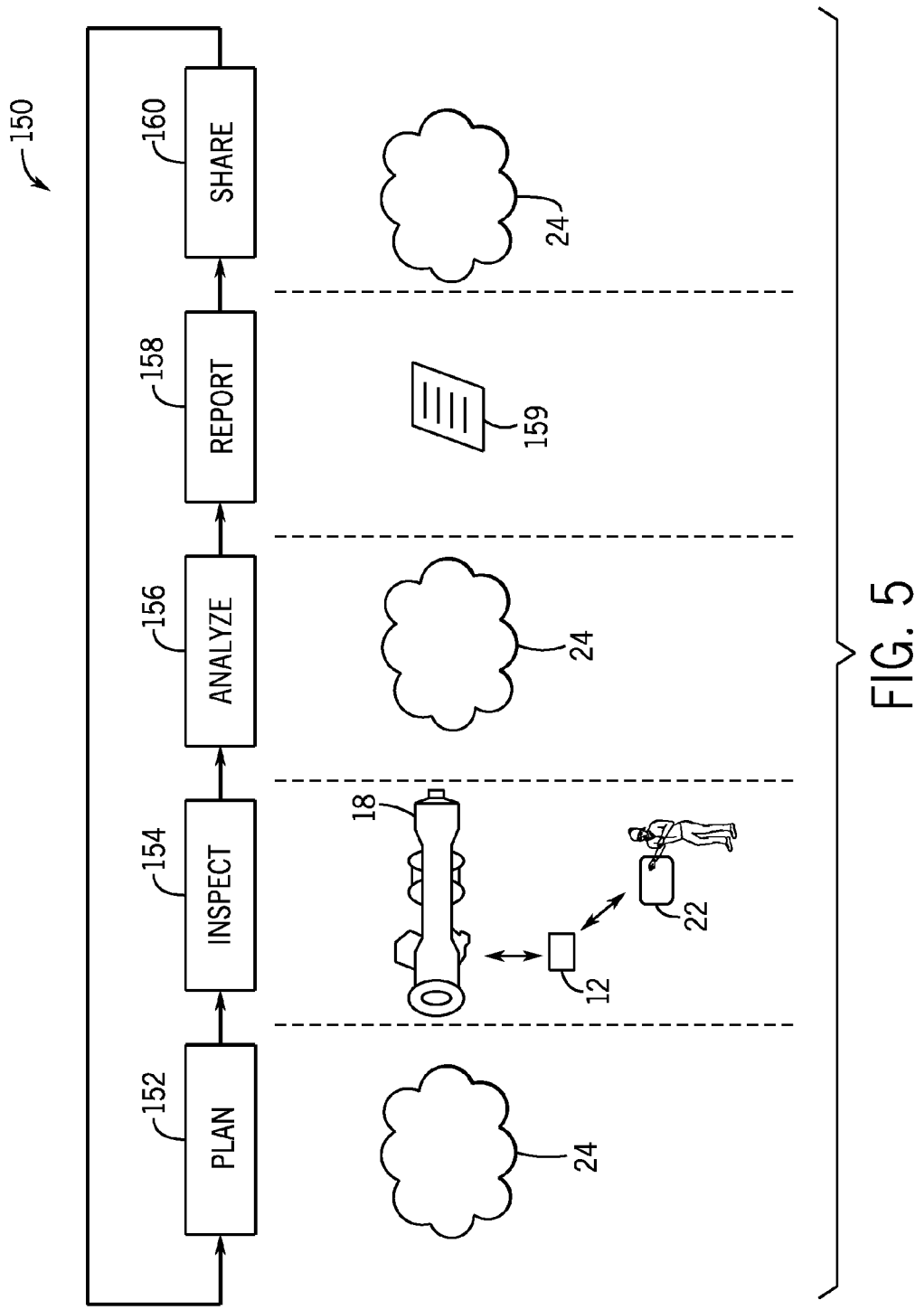
FIG. 5 is a flowchart illustrating an embodiment of a process useful in using the distributed NDT system for planning, inspecting, analyzing, reporting, and sharing of data, such as inspection data.

FIG. 5 is a flowchart of an embodiment of a process 150 suitable for planning, inspecting, analyzing, and/or sharing a variety of data by using the aforementioned devices 12, 14, 16, 22, 92, 94, 96, and the cloud 24. Indeed, the techniques described herein may use the devices 12, 14, 16, 22, 92, 94, 96 to enable processes, such as the depicted process 150, to more efficiently support and maintain a variety of equipment. In certain embodiments, the process 150 or portions of the process 150 may be included in non-transitory computer-readable media stored in memory, such as the memory 15, 19, 23, 93, 97, 101 and executable by one or more processors, such as the processors 17, 21, 25, 95, 99, 103.

In one example, the process 150 may plan (block 152) for inspection and maintenance activities. Data acquired by using the devices 12, 14, 16, 22, 42, 44, 46, an others, such as fleet data acquired from a fleet of turbomachinery 18, from equipment users (e.g., aircraft 104 service companies), and/or equipment manufacturers, may be used to plan (block 152) maintenance and inspection activities, more efficient inspection schedules for machinery, flag certain areas for a more detailed inspection, and so on. The process 150 may then enable the use of a single mode or a multi-modal inspection (block 154) of desired facilities and equipment (e.g., turbomachinery 18). As mentioned above, the inspection (block 154) may use any one or more of the NDT inspection devices 12 (e.g., borescope 14, PTZ camera 16, eddy current inspection device 92, ultrasonic flaw detector 94, digital radiography device 96), thus providing with one or more modes of inspection (e.g., visual, ultrasonic, eddy current, x-ray). In the depicted embodiment, the mobile device 22 may be used to remote control the NDT inspection devices 12, to analyze data communicated by the NDT inspection devices 12, to provide for additional functionality not included in the NDT inspection devices 12 as described in more detail herein, to record data from the NDT inspection devices 12, and to guide the inspection (block 154), for example, by using menu-driven inspection (MDI) techniques, among others.

Results of the inspection (block 154), may then be analyzed (block 156), for example, by using the NDT device 12, by transmitting inspection data to the cloud 24, by using the mobile device 22, or a combination thereof. The analysis may include engineering analysis useful in determining remaining life for the facilities and/or equipment, wear and tear, corrosion, erosion, and so forth. The analysis may additionally include operations research (OR) analysis used to provide for more efficient parts replacement schedules, maintenance schedules, equipment utilization schedules, personnel usage schedules, new inspection schedules, and so on. The analysis (block 156) may then be reported (block 158), resulting in one or more reports 159, including reports created in or by using the cloud 24, detailing the inspection and analysis performed and results obtained. The reports 159 may then be shared (block 160), for example, by using the cloud 24, the mobile device 22, and other techniques, such as workflow sharing techniques. In one embodiment, the process 150 may be iterative, thus, the process 150 may iterate back to planning (block 152) after the sharing (block 160) of the reports 159. By providing for embodiments useful in using the devices (e.g., 12, 14, 16, 22, 92, 94, 96) described herein to plan, inspect, analyze, report, and share data, the techniques described herein may enable a more efficient inspection and maintenance of the facilities 20, 106 and the equipment 18, 104. Indeed, the transfer of multiple categories of data may be provided, as described in more detail below with respect to FIG. 6.

Figure 6:
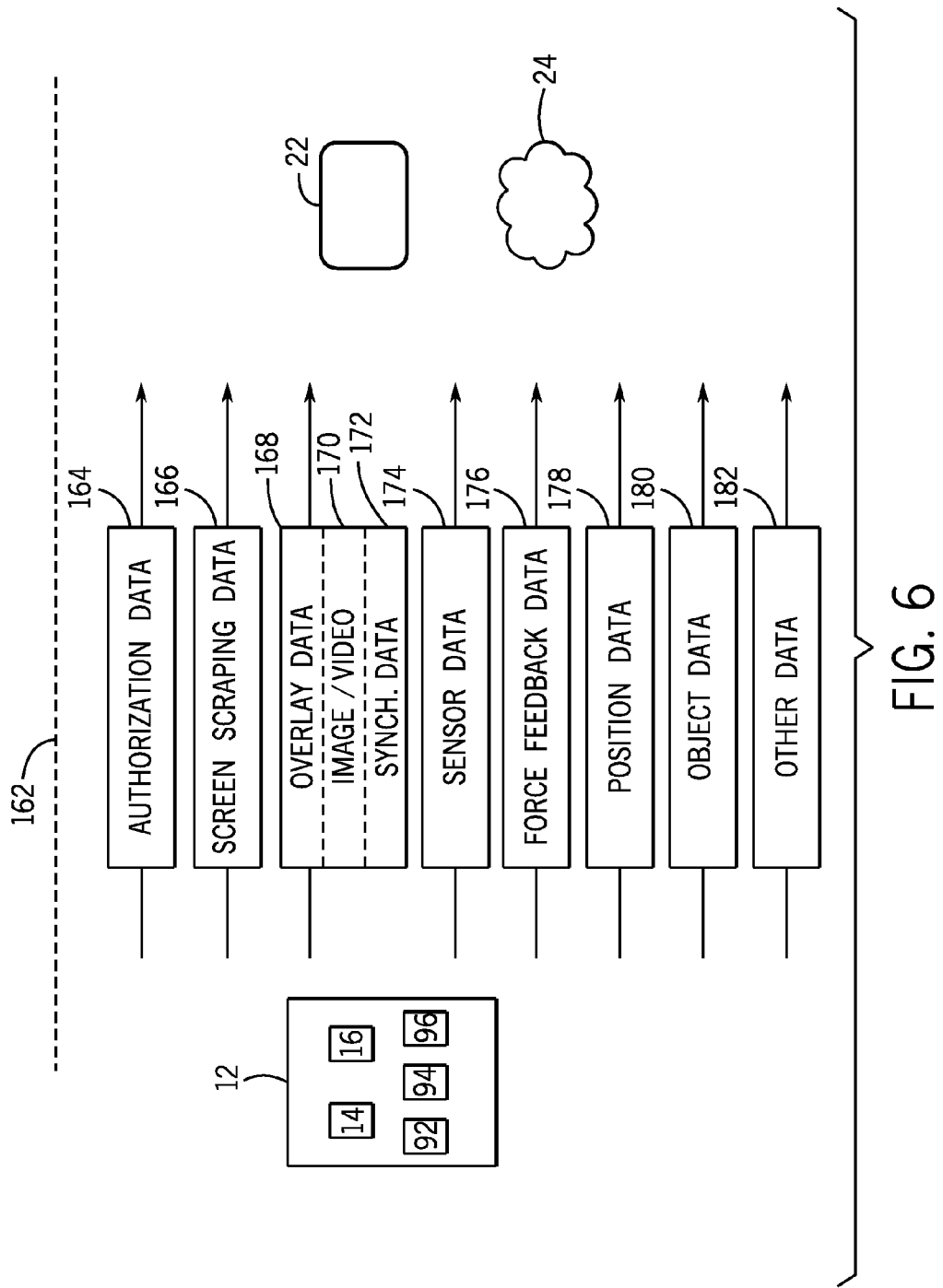
FIG. 6 is a block diagram of an embodiment of information flow through a wireless conduit.

FIG. 6 is a data flow diagram depicting an embodiment of the flow of various data categories originating from the NDT inspection devices 12 (e.g., devices 14, 16, 92, 94, 96) and transmitted to the mobile device 22 and/or the cloud 24. As mentioned above, the NDT inspection devices 12 may use a wireless conduit 162 to transmit the data. In one embodiment, the wireless conduit 112 may include WiFi (e.g., 802.11x), cellular conduits (e.g., HSPA, HSPA+, LTE, WiMax), NFC, Bluetooth, PANs, and the like. The wireless conduit 162 may use a variety of communication protocols, such as TCP/IP, UDP, SCTP, socket layers, and so on. In certain embodiments, the wireless conduit 162 may include secure layers, such as SSL, VPN layers, encrypted layers, challenge key authentication layers, token authentication layers, and so on. Accordingly, an authorization data 164 may be used to provide any number of authorization or login information suitable to pair or otherwise authenticate the NDT inspection device 12 to the mobile device 22 and/or the cloud 24. Additionally, the wireless conduit 162 may dynamically compress data, depending on, for example, currently available bandwidth and latency. The mobile device 22 may then uncompress and display the data. Compression/decompression techniques may include H.261, H.263, H.264, moving picture experts group (MPEG), MPEG-1, MPEG-2, MPEG-3, MPEG-4, DivX, and so on.

In certain modalities (e.g., visual modalities), images and video may be communicated by using certain of the NDT inspection devices 12. Other modalities may also send video, sensor data, and so on, related to or included in their respective screens. The NDT inspection device 12 may, in addition to capturing images, overlay certain data onto the image, resulting in a more informative view. For example, a borescope tip map may be overlaid on the video, showing an approximation of the disposition of a borescope tip during insertion so as to guide the operator 26 to more accurately position the borescope camera 126. The overlay tip map may include a grid having four quadrants, and the tip 136 disposition may be displayed as dot in any portion or position inside of the four quadrants. A variety of overlays may be provided, as described in more detail below, including measurement overlays, menu overlays, annotation overlays, and object identification overlays. The image and video data, such as the video 84, may then be displayed, with the overlays generally displayed on top of the image and video data.

In one embodiment, the overlays, image, and video data may be "screen scraped" from the screen 135 and communicated as screen scrapping data 166. The screen scrapping data 166 may then be displayed on the mobile device 22 and other display devices communicatively coupled to the cloud 24. Advantageously, the screen scrapping data 166 may be more easily displayed. Indeed, because pixels may include both the image or video and overlays in the same frame, the mobile device 22 may simply display the aforementioned pixels. However, providing the screen scraping data may merge both the images with the overlays, and it may be beneficial to separate the two (or more) data streams. For example, the separate data streams (e.g., image or video stream, overlay stream) may be transmitted approximately simultaneously, thus providing for faster data communications. Additionally, the data streams may be analyzed separately, thus improving data inspection and analysis.

Accordingly, in one embodiment, the image data and overlays may be separated into two or more data streams 168 and 170. The data stream 168 may include only overlays, while the data stream 170 may include images or video. In one embodiment, the images or video 170 may be synchronized with the overlays 168 by using a synchronization signal 172. For example, the synchronization signal may include timing data suitable to match a frame of the data stream 170 with one or more data items included in the overlay stream 168. In yet another embodiment, no synchronization data 172 data may be used. Instead, each frame or image 170 may include a unique ID, and this unique ID may be matched to one or more of the overlay data 168 and used to display the overlay data 168 and the image data 170 together.

The overlay data 168 may include a tip map overlay. For example, a grid having four squares (e.g., quadrant grid) may be displayed, along with a dot or circle representing a tip 136 position. This tip map may thus represent how the tip 136 is being inserted inside of an object. A first quadrant (top right) may represent the tip 136 being inserted into a top right corner looking down axially into the object, a second quadrant (top left) may represent the tip 136 being inserted into a left right corner looking down axially, a third quadrant (bottom left) may represent the tip 136 being inserted into a bottom left corner, and a fourth quadrant (bottom right) may represent the tip 136 being inserted into a bottom right corner. Accordingly, the borescope operator 26 may more easily guide insertion of the tip 136.

The overlay data 168 may also include measurement overlays. For example, measurement such as length, point to line, depth, area, multi-segment line, distance, skew, and circle gauge may be provided by enabling the user to overlay one or more cursor crosses (e.g., "+") on top of an image. In one embodiment a stereo probe measurement tip 136, or a shadow probe measurement tip 136 may be provided, suitable for measurements inside of objects, including stereoscopic measurements and/or by projecting a shadow onto an object. By placing a plurality of cursor icons (e.g., cursor crosses) over an image, the measurements may be derived using stereoscopic techniques. For example, placing two cursors icons may provide for a linear point-to-point measurement (e.g., length). Placing three cursor icons may provide for a perpendicular distance from a point to a line (e.g., point to line). Placing four cursor icons may provide for a perpendicular distance between a surface (derived by using three cursors) and a point (the fourth cursor) above or below the surface (e.g., depth). Placing three or more cursors around a feature or defect may then give an approximate area of the surface contained inside the cursors. Placing three or more cursors may also enable a length of a multi-segment line following each cursor.

Likewise, by projecting a shadow, the measurements may be derived based on illumination and resulting shadows. Accordingly, by positioning the shadow across the measurement area, then placing two cursors as close as possible to the shadow at furthermost points of a desired measurement may result in the derivation of the distance between the points. Placing the shadow across the measurement area, and then placing cursors at edges (e.g., illuminated edges) of the desired measurement area approximately to the center of a horizontal shadow may result in a skew measurement, otherwise defined as a linear (point-to-point) measurement on a surface that is not perpendicular to the probe 14 view. This may be useful when a vertical shadow is not obtainable.

Similarly, positioning a shadow across the measurement area, and then placing one cursor on a raised surface and a second cursor on a recessed surface may result in the derivation of depth, or a distance between a surface and a point above or below the surface. Positioning the shadow near the measurement area, and then placing a circle (e.g., circle cursor of user selectable diameter, also referred to as circle gauge) close to the shadow and over a defect may then derive the approximate diameter, circumference, and/or area of the defect.

Overlay data 168 may also include annotation data. For example, text and graphics (e.g. arrow pointers, crosses, geometric shapes) may be overlaid on top of an image to annotate certain features, such as "surface crack." Additionally, audio may be captured by the NDT inspection device 12, and provided as an audio overlay. For example, a voice annotation, sounds of the equipment undergoing inspection, and so on, may be overlaid on an image or video as audio. The overlay data 168 received by the mobile device 22 and/or cloud 24 may then be rendered by a variety of techniques. For example, HTML5 or other markup languages may be used to display the overlay data 168. In one embodiment, the mobile device 22 and/or cloud 24 may provide for a first user interface different from a second user interface provided by the NDT device 12. Accordingly, the overlay data 168 may be simplified and only send basic information. For example, in the case of the tip map, the overlay data 168 may simply include X and Y data correlative to the location of the tip, and the first user interface may then use the X and Y data to visually display the tip on a grid.

Additionally sensor data 174 may be communicated. For example, data from the sensors 126, 140, and x-ray sensor data, eddy current sensor data, and the like may be communicated. In certain embodiments, the sensor data 174 may be synchronized with the overlay data 168, for example, overlay tip maps may be displayed alongside with temperature information, pressure information, flow information, clearance, and so on. Likewise, the sensor data 174 may be displayed alongside the image or video data 170.

In certain embodiments, force feedback or haptic feedback data 176 may be communicated. The force feedback data 176 may include, for example, data related to the borescope 14 tip 136 abutting or contacting against a structure, vibrations felt by the tip 136 or vibration sensors 126, force related to flows, temperatures, clearances, pressures, and the like. The mobile device 22 may include, for example, a tactile layer having fluid-filled microchannels, which, based on the force feedback data 176, may alter fluid pressure and/or redirect fluid in response. Indeed, the techniques describe herein, may provide for responses actuated by the mobile device 22 suitable for representing sensor data 174 and other data in the conduit 162 as tactile forces.

The NDT devices 12 may additionally communicate position data 178. For example, the position data 178 may include locations of the NDT devices 12 in relation to equipment 18, 104, and/or facilities 20, 106. For example, techniques such as indoor GPS, RFID, triangulation (e.g., WiFi triangulation, radio triangulation) may be used to determine the position 178 of the devices 12. Object data 180 may include data related to the object under inspection. For example, the object data 180 may include identifying information (e.g., serial numbers), observations on equipment condition, annotations (textual annotations, voice annotations), and so on. Other types of data 182 may be used, including but not limited to menu-driven inspection data, which when used, provides a set of pre-defined "tags" that can be applied as text annotations and metadata. These tags may include location information (e.g., $1^{st}$ stage HP compressor) or indications (e.g., foreign object damage) related to the object undergoing inspection. Other data 182 may additionally include remote file system data, in which the mobile device 22 may view and manipulate files and file constructs (e.g., folders, subfolders) of data located in the memory 25 of the NDT inspection device 12. Accordingly, files may be transferred to the mobile device 22 and cloud 24, edited and transferred back into the memory 25. By communicating the data 164-182 to the mobile device 22 and the cloud 24, the techniques described herein may enable a faster and more efficient process 150.

Figure 7:
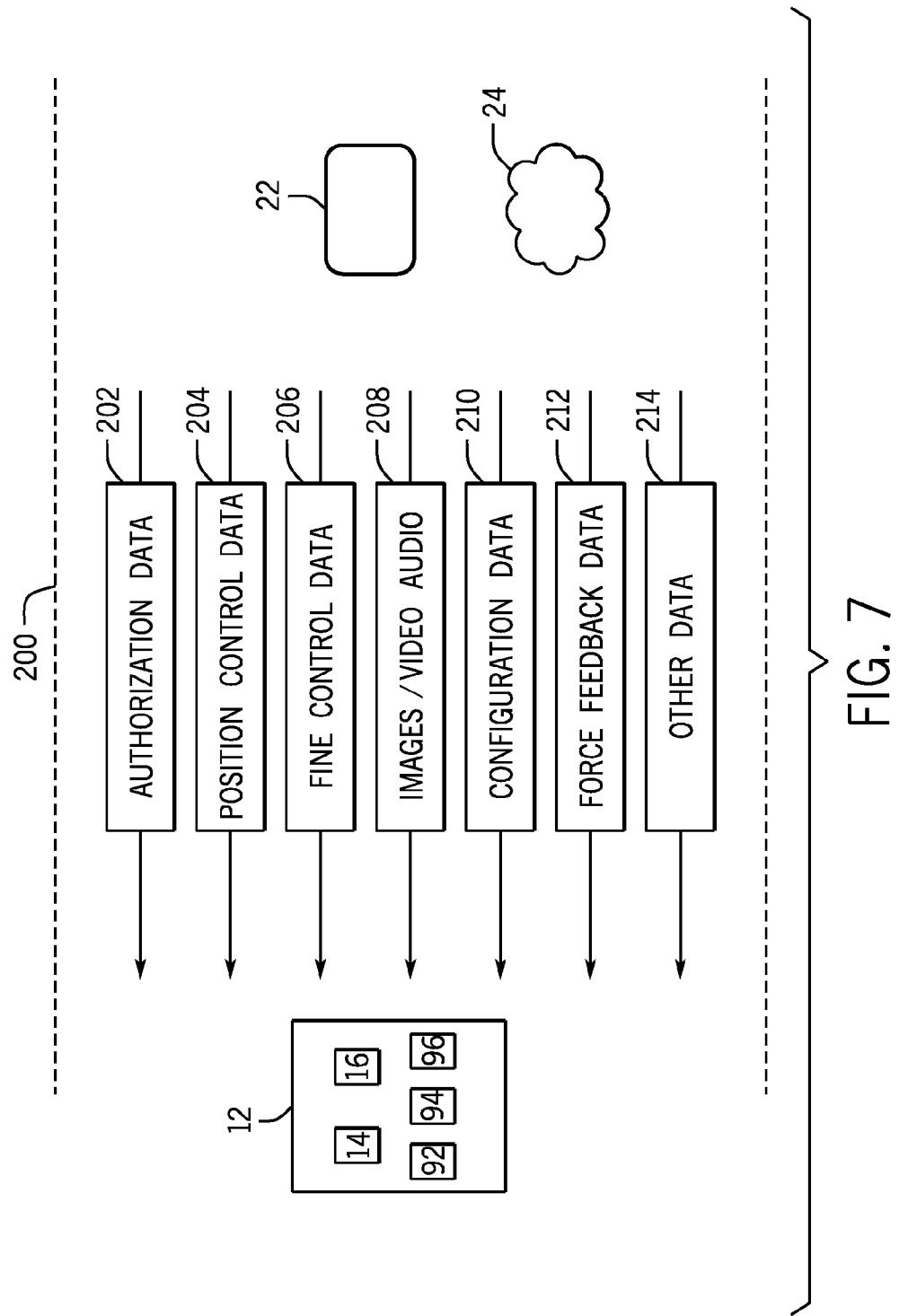
FIG. 7 is a block diagram of an embodiment of information flow through a wireless conduit of information useful in remote control of the NDT inspection system of FIG. 1.

Turning now to FIG. 7, the figure is a data flow diagram illustrating an embodiment of the flow of various data categories originating from the mobile device 22, devices inside the cloud 24, and/or devices communicatively connected to the cloud 24 (e.g., computing system 29) and directed, for example, towards the NDT inspection devices 12 (e.g., borescope 14, PTZ camera 16, eddy current inspection device 92, ultrasonic flaw detector 94, digital radiography device 96). Such data may include control data suitable for controlling the NDT device. As described herein, the control of the NDT inspection devices 12 includes both control of positioning apparatus, such as the articulating section 122 of the borescope 14, apparatus used to pan, tilt, and zoom the PTZ camera 16, as well as the remote control of file systems in the NDT devices 12, screen(s) included in the NDT devices 12, and the setting of parameters used to operate or to configure the NDT devices 12, as described in more detail below.

In the depicted embodiment, a wireless conduit 200 may be used to communicate the data (e.g. control data) to the NDT devices 12. Similar to the conduit 162, the wireless conduit, in certain embodiments, may include WiFi (e.g., 802.11x), cellular conduits (e.g., HSPA, HSPA+, LTE, WiMax), NFC, Bluetooth, PANs, and the like. The wireless conduit 162 may use a variety of communication protocols, such as TCP/IP, UDP, SCTP, socket layers, and so on. In certain embodiments, the wireless conduit 162 may include secure layers, such as SSL, VPN layers, encrypted layers, challenge key authentication layers, token authentication layers, and so on. It is to be noted that, in other embodiments, wired conduits may be used alternative to or in lieu of the wireless conduits 162, 200.

Authorization data 202 may be communicated, and used, for example, in conjunction with the authorization data 164 to enable secure access to the NDT devices 12. A variety of secure authentication techniques may be used, including but not limited to login/password combinations, maintaining a list of secure MAC addresses, challenge-response authentication between two or more of the devices 12, 22, and cloud 24, secure NFC authentication, using a third-party authentication server (e.g., by using certificate authentication, key exchange authentication), and so on.

Position control data 204 may additionally be communicated, useful to move or otherwise position components of the NDT devices 12. Indeed, certain components of the NDT devices 12 may be physically moved remotely by using, for example, a virtual joystick described in more detail below with respect to FIG. 8. Any number of systems (e.g., mobile devices 22, computing systems 29, web-based virtual controllers), such as devices connected to the NDT devices 12 locally (e.g., WiFi, Bluetooth) and/or via the cloud 24, may be used to remotely communicate the data 204 and used to remotely position components of the NDT devices 12.

Advantageously, a variety of remote operations, training, and collaboration may be enabled. For example, an expert operator may train a new borescope operator on the job. The new borescope operator may hold the borescope 14 and observe while the expert operator controls the borescope 14 by using the mobile device 22. The expert operator may then point out tip control techniques, relate what type of observations are correlative to corrosion, show how to make annotations, and so on. In other cases, the expert operator may be located at a different geographic location and may collaborate and/or train the new borescope operator by the use of VOIP, whiteboarding, and the like, or may use the mobile device 22 to perform a full inspection remotely. In another training example, the new borescope operator may be using the mobile device 22 and/or borescope 14, and receive training from remote locations, such as web-based locations. For example, the screen 137 of the mobile device 22 may be portioned into multiple viewing areas (e.g., "splitscreens") so that one viewing area shows borescope 14 images or video while a second viewing area shows a training video, and a third area shows an online equipment manual procured wirelessly. Indeed, the borescope 14 may receive data, including targeted multimedia inspection data from external sources (e.g., mobile device 22, cloud 24, computing system 29).

Additionally, fine control data 206 may be communicated. For example, "jogging" data suitable for moving the borescope's articulating section 122 and/or the PTZ camera 16 at smaller increments than the position control data 204. More specifically, the fine control data 206 may include a step to move (e.g., 0.5 mm, between 0.05 mm and 1 cm or more), and a number of steps to move (e.g., 1, 2, 3, 4, 5 or more). Accordingly, components of the NDT device 12 may be more precisely disposed to better observe certain features undergoing inspection. The position control data 204 and fine control data 206 may be produced by virtual controllers or physical controllers communicatively connected to the NDT devices 12.

Images, video, text, and/or audio data 208 may be additionally communicated. For example, the mobile device 22, the cloud 24, and/or devices coupled to the cloud (e.g., computing system 29) may send images and/or video, as well as overlay annotations useful in illustrating to the borescope operator certain features to inspect further, along with audio detailing explanations of how to proceed with the inspection. In certain embodiments, the data 208 may be training data useful in detailing inspection procedures. In other embodiment, the data 208 may include data transmitted from experts, detailing instructions on how to more thoroughly inspect certain equipment. In yet another embodiment, the data 208 may include data sent through automated entities (e.g., expert systems, fuzzy logic systems, neural network systems, state vector machines) based on received data from FIG. 6 useful in directing and/or focusing the inspection after automatically analyzing the received data.

Configuration data 210 may also be communicated. For example data used to update file systems included in the NDT devices 12, to reprogram the NDT devices 12, to set parameters useful in operating the NDT devices 12, and/or to reconfigure electronic components of the device 12 (e.g., flash upgrade) may be sent to the NDT inspection devices 12 remotely. Indeed, programming and parameter-setting may be done remotely, thus providing for techniques to more easily maintain the NDT devices up to date, and to improve device operations. It is to be understood that different NDT devices 12 may use different parameter sets. As a non-limiting example only, some parameters useful to remote control the NDT devices 12 may include parameters for starting acquisition of data, stopping acquisition of data, saving file, naming or renaming a file, adjusting a gain, adjusting a time base, compensating for lift off—zeroing signal during eddy current inspection, adjusting phase rotation, adjusting persistence, balancing a probe, adjusting gate (e.g., amplitude adjustment, position adjustment), adjusting color palette—soft gain, changing signal rectification, changing pulser filter, zooming in and out, adjusting a pulse width, adjusting a data filter (e.g., bandwidth), adjusting pulse repetition frequency, adjusting sweep angle start/stop, adjusting sweep angle increment, turning channels on/off, freezing data, clearing/erasing data, adjusting span, adjusting filters, changing spot positions, changing display types (e.g., spot display, timebase display, waterfall display), and/or changing channel views.

In one embodiment, client-server techniques, such as virtual network computing (VNC), remote desktop protocol (RDP), desktop sharing, among others, may be used to send configuration data 210 and receive data correlative with screen control of the NDT devices 12. Likewise, remote file system control may be provided by using techniques such as secure file transfer protocol (ftp), ftp over secure shell (SSH), remote file sharing (RFS), and/or distributed file systems (e.g., using the cloud 24 to store and retrieve files through the NDT devices 12). Files may be added, renamed, deleted, and/or updated. Likewise, file folders and other file storage structures may be similarly renamed, deleted, and/or updated.

Force feedback data 212 may additionally be communicated. For example, a more forceful push onto the mobile device's 22 touchscreen may translate into data 212 useful in moving the borescope's articulating section 122 more quickly. Likewise, a haptic controller may be coupled to the computing device 29 and provide the force feedback data. The more force applied, the faster the correlative movement of components such as the articulating section 122 of the borescope 14. It is to be noted that force feedback data 212 may be provided by other devices, such as the physical joystick 131, a virtual joystick described in more detail with respect to FIG. 8 below, haptic controllers wirelessly coupled to the NDT devices 12, including controllers coupled through the cloud 24 or mobile device 22 (e.g., when the mobile device 22 is providing for WAP functionality). Other data 214 may include updated digital manuals or help manuals useful in operating the NDT devices 12, manuals relating to the equipment (e.g., turbomachinery 18, aircraft 54) undergoing inspection, and so on. Accordingly, the wireless conduit 200 would be used to communicate and to change or otherwise modify NDT device 12 information, such as borescope-specific information including but not limited to measurement information (cursor placement, measurements, stereo matches), MDI information (current stage, asset information, reference material), current menu selections, tip temperatures/pressures, tip orientation (tip map, artificial horizon), 3DPM range indication, text annotation, and so on. Software control applications may render native graphics with touchscreen buttons or softkey labels as described in more detail below, and if appropriate, accept user input. Hard physical buttons with either fixed or dynamic functionality can also be used to accept input. It is to be noted that the NDT device 12 may be controlled by a first entity (or more than one remote entities) at the same time as the NDT device 12 is used by a second entity. Indeed, the control embodiments described herein enable multiple parties to control the device at the same time, including multiple remote parties.

Figure 8:
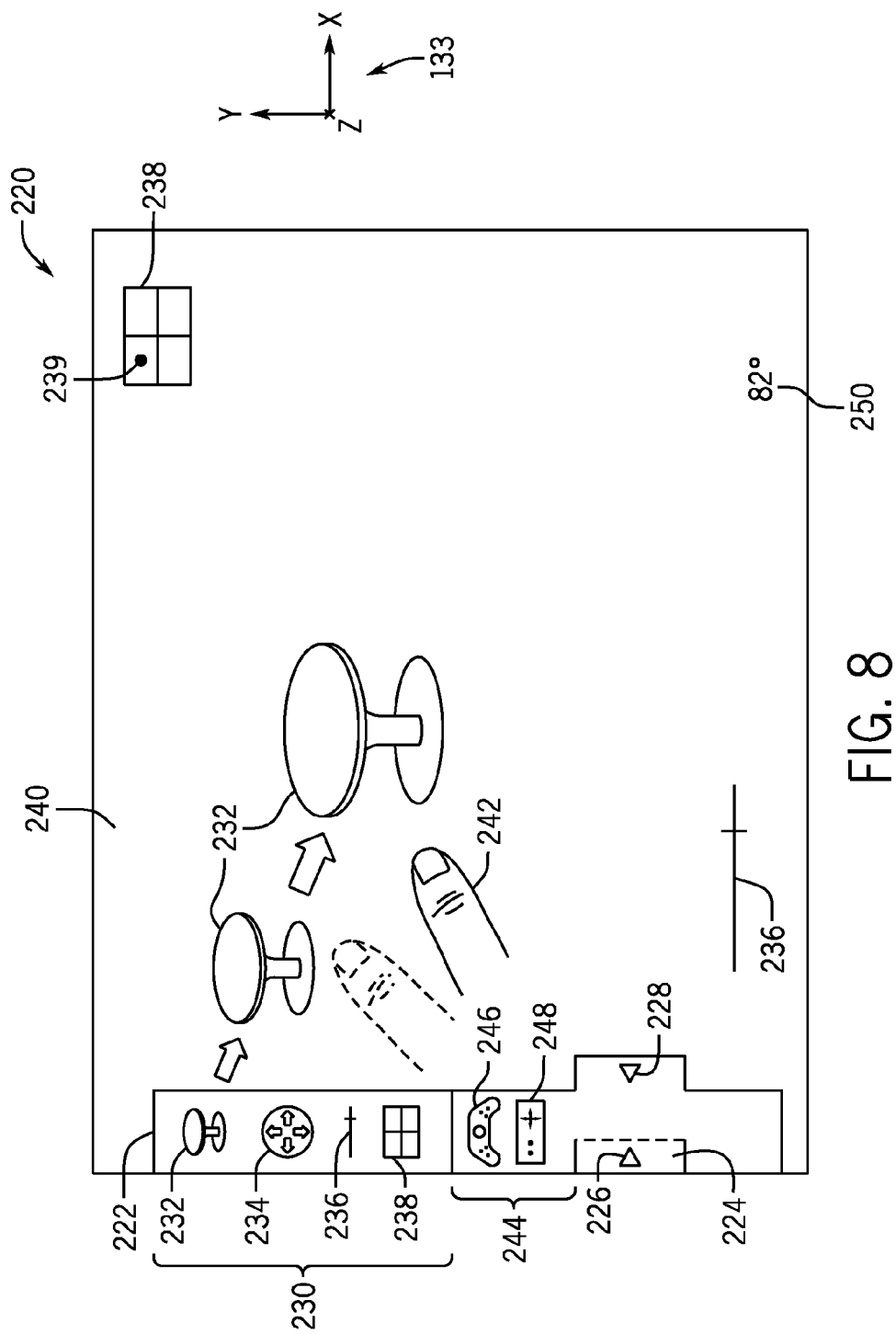
FIG. 8 is a screen view of an embodiment of a virtual joystick.

FIG. 8 is illustrative of an embodiment of a screen view 220 useful in remote controlling the NDT devices 12. The screen view 220 may be included in the mobile device 22 (e.g., tablet, cell phone, notebook touchscreen). The screen view 220 may be implemented by using non-transitory computer-readable instructions stored, for example, in the memory 25 of the mobile device 22. In the depicted embodiment, an interface bar 222 may be activated, for example, by "swiping" a tab control 224. Once activated, the tab control 224 may change icons, from a right arrow icon 226 to a left arrow icon 228, denoting preferred swiping direction.

In a section 230 of the interface bar 222, a plurality of virtual controls may be displayed. The depicted virtual controls include a virtual joystick 232, a virtual control pad 234, a slider 236, and a tip map 238 showing a position 239 of the tip 136. Other virtual controls may be provided, as described in more detail below with respect to FIG. 9. The virtual controls may be displayed on a screen 240 of a control software application executable, for example, by the processor 23 of the mobile device 22, and used to control one or more components of the NDT devices 12. In the depicted example, a finger 242 is used to move the virtual joystick 232 into a desired location. Indeed, all of the virtual controls 234, 236, 238 may be similarly disposed onto any area of the screen 240. The virtual controls 232, 234, 236, 238 are resizable. Additionally, techniques such as "pinch-to-zoom," may be used to resize the controls 232, 234, 236, 238 to a desired size.

Once the virtual controls are positioned into desired locations of the screen 240, a section 244 of the screen may store a customized template 246 that include the saved positions and sizes for the screen 240 controls. Other templates 248 may be provided, for example, via the cloud 24, from a variety of sources, including the manufacturer for the NDT devices 12, equipment 18, 54 manufacturers, shops that service the equipment 18, 54, software vendors, and the like. The templates 248 may store a plurality of virtual controls and certain placement and sizes originally provided by the template 248. In certain embodiments, the template(s) 248 may be downloaded automatically based on the type of NDT device 12 selected (e.g., 14, 16, 92, 94, 96), the location of the NDT device 12, such as proximity to a specific model and/or serial number of the equipment 18, 54. Indeed, control templates 248 specific to certain equipment and/or facilities may be automatically downloaded based on the selected NDT device 12 and/or proximity of the NDT device 12 to the aforementioned equipment or facility.

In the depicted example of the screen 240, the virtual joystick 232 may be used to control the articulating section 122 of the borescope 14. The tip map 238 may then be used to show a location of the tip 136 when disposed inside of the equipment undergoing inspection. Lights 128, 138 may be controlled by using the slider 236, and a temperature may be displayed by using a text control 250. The entirety of the screen 240, or a portion of the screen 240, may then be used to display an image or video captured, for example, by using the borescope camera 126 or the camera 16. By providing for dynamic, reconfigurable screens 240, the techniques described herein may enable a more efficient and thorough inspection 154.

Figure 9:
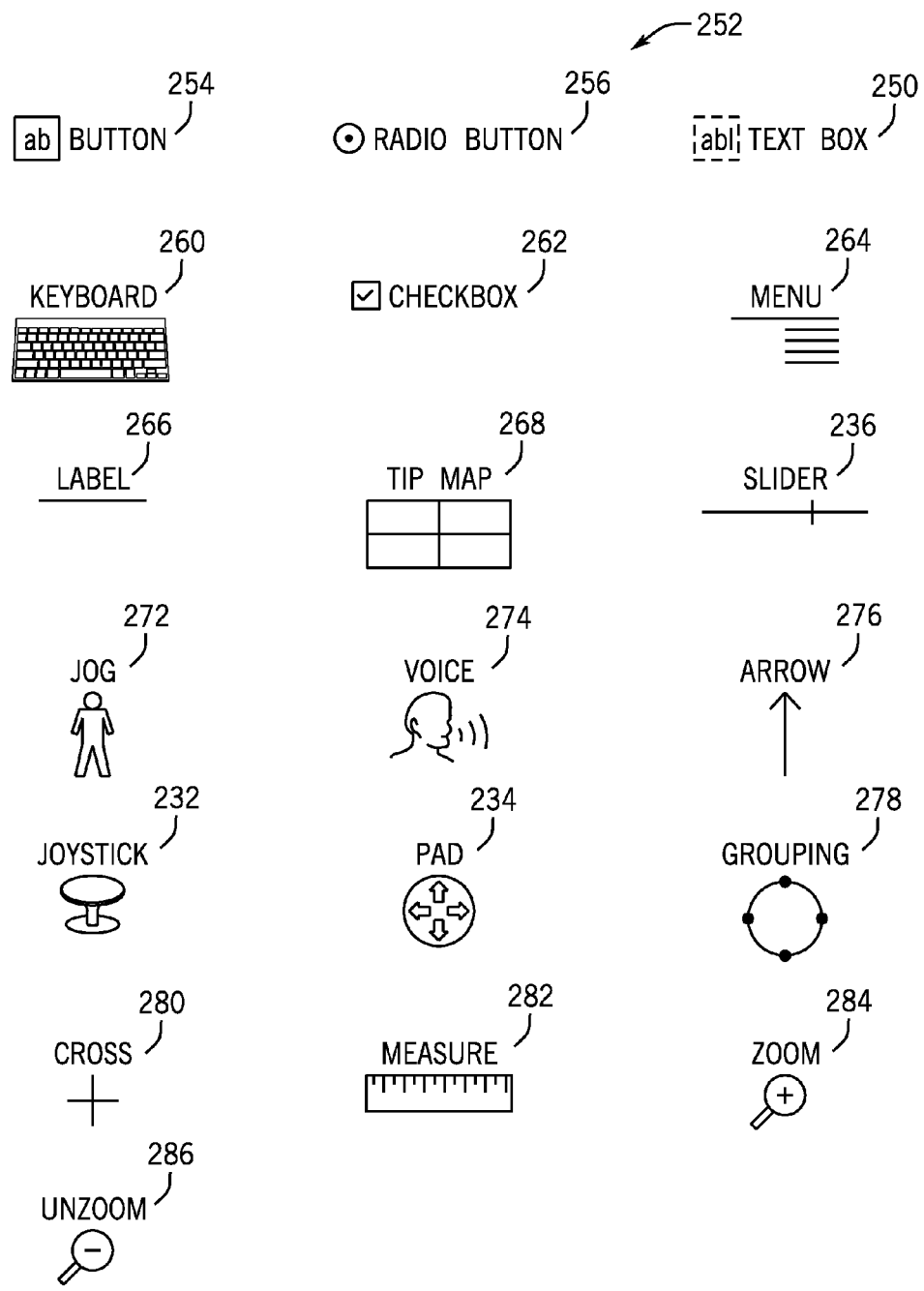
FIG. 9 is a view of embodiments of a plurality of virtual controls.

Turning to FIG. 9, the figure depicts a non-exhaustive list of embodiments of virtual controls that may be disposed on the screen 240 of FIG. 8. For example, a button control 254 may be used to activate or deactivate components (hardware or software components) of the NDT device 12 and/or mobile device 22. A radio button 256 may be used to select or deselect components of the NDT device 12 and/or mobile device 22. The textbox control 250, also shown in FIG. 8, may be used to display any number of textual data (e.g., sensor data, annotations, notes, time/date, parameter settings, and so on). A keyboard control 260 may be used to display a virtual keyboard suitable for the typing of data. A checkbox control 262 may be used to check or uncheck features (hardware or software features) of the NDT device 12 and/or mobile device 22. A menu control 264 may be used to display MDI data and other menu related data. A label control 266 may be used to display a static text or graphic label, as desired. A tip map control 268 may be used to display a current tip 136 position.

Likewise, the slider control 236 (also shown in FIG. 8) may be used to adjust any number of hardware or software components, parameters, and so on by "sliding" to a desired level. A jog control 272 may be used to "jog" the fine control data 206, or to set properties associated with the fine control data 206 (e.g., steps to move, number of steps to move). A voice control 274 may be used to provide voice commands, voice annotations, VOIP conversations, and so on. An arrow control 276 may be used to point to image or video features. The joystick 232 and control pad 234 (also shown in FIG. 8) may be used to manipulate certain components (e.g., articulating section 122 of the borescope 14) to dispose the components into a desired position.

Similarly, a grouping control 278 may be used to "lasso" or group components in order to move the components, delete the components from the screen 240, and so on. A cross 280 cursor may be used to mark or otherwise indicate certain locations on the screen 240 correlative with features of an image or video. A measure component 282 may then use, for example, the one or more crosses 280 to derive measurements, such as the stereoscopic and/or shadow measurements described above with respect to FIG. 6. Zoom controls 284 and unzoom controls 286 may be used to zoom into or out of certain portions (or all) of the screen 240. By providing for resizable, repositionable virtual controls 252, the techniques described herein may enable a more efficient use of space of the screen 240, and provide for customizable, dynamic screens 240.

Figure 10:
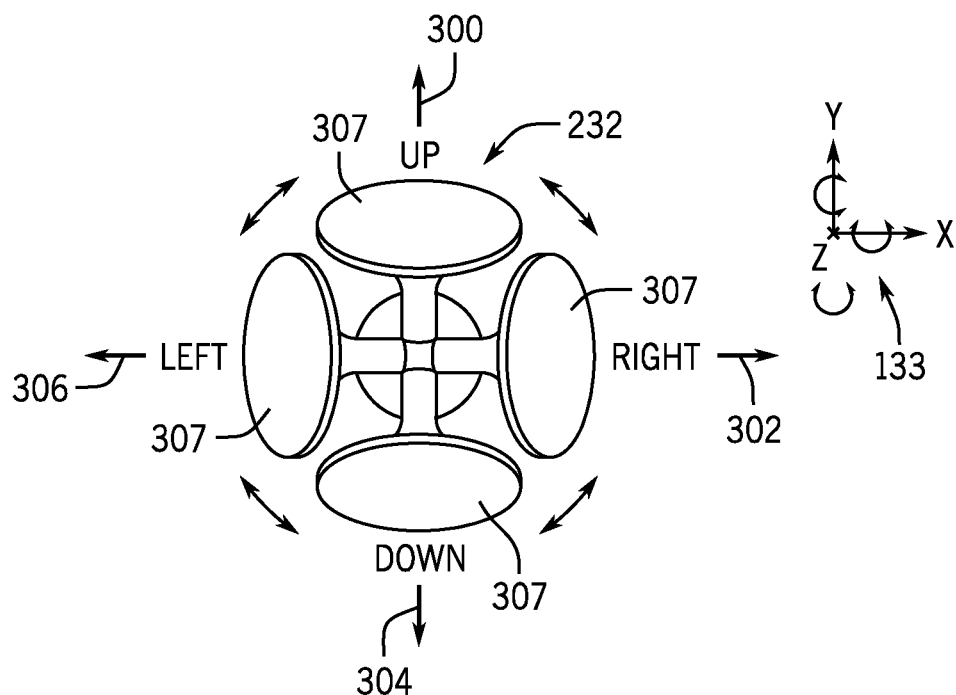
FIG. 10 is a view of a plurality of positions for the virtual joystick of FIG. 8, in accordance with one embodiment.

Some of the controls, such as the virtual joystick 232, may be disposed in a variety of orientations as shown in an embodiment illustrated in FIG. 10. In the depicted embodiment, the virtual joystick 232 is shown in four different orientations 300, 302, 304, and 306. More specifically, the orientation 300 positions the joystick 232 parallel to the Y axis with a joystick head 307 in an "up" position, the orientation 302 positions the joystick 232 parallel to the X axis with the joystick head 307 in a "left" position, the orientation 304 positions the joystick 232 parallel to the Y axis with the joystick head 307 in a "down" position, and the orientation 306 positions the joystick 232 parallel to the X axis with the joystick head 307 in a "left" position. Other orientations may be chosen to position the virtual joystick 232, for example, orientations parallel to the Z-axis, or at any angle with respect to the XY plane, XZ plane, and or YZ plane. Additionally, the virtual joystick 232 and/or virtual control pad 234 may be adjusted to vary a sensitivity of manipulation. That is, when using the touchscreen 135, 137, it may be useful to allow user control of the sensitivity of the joystick, such that the user may configure what level of touch or movement is desired to "move" the virtual control (e.g., 232, 234) a given amount. Accordingly, the joystick 232 may provide for a more flexible interface useful in controlling a variety of NDT devices 12.

Figure 11:
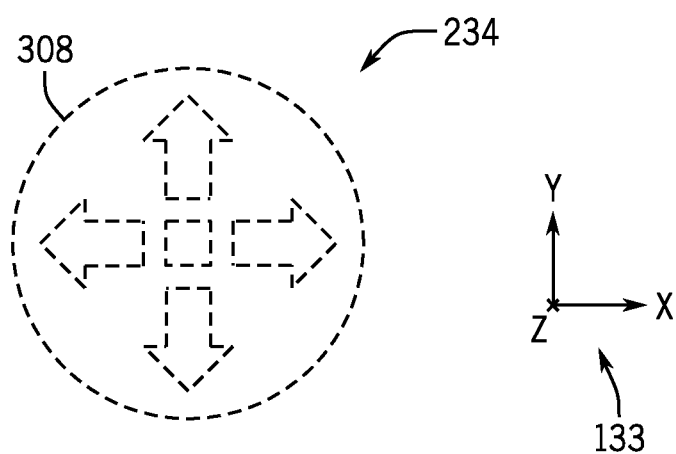
FIG. 11 is a view of an embodiment of a translucent control pad.

In some embodiments, such as the embodiment depicted in FIG. 11, the virtual controls shown in FIG. 9 may be displayed as opaque or translucent visualizations. For example, the control pad 234 is shown as having a transparent body with certain features 308 visualized in outline form. By providing for opaque or translucent visualizations, images or video displayed underneath the controls of FIG. 9 may be more easily viewed, and the inspection 154 may be more easily performed.

Figure 12:
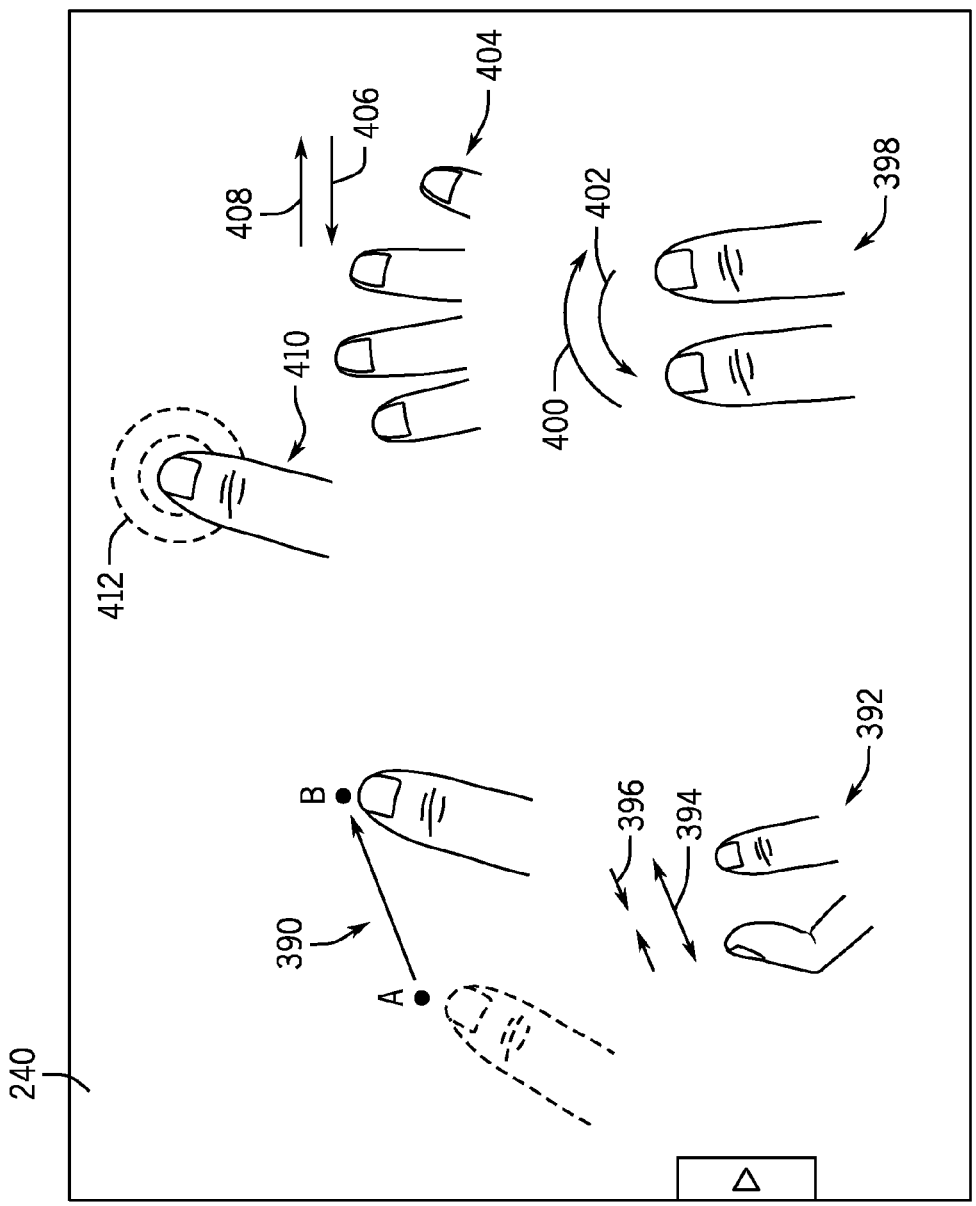
FIG. 12 is a view of a plurality of gesture controls, in accordance with one embodiment.

In some cases, it may be desirable to control to the NDT devices 12 by using gesture control in lieu of the joystick 232 or the control pad 234, or additional to the controls 232, 234. Accordingly, screen 240 space may be maximized. FIG. 12 depicts a non-inclusive example of embodiments of a plurality of gestures that may be used to control the NDT devices 12. A single digit or finger gesture 390 may be used to define a vector AB with a starting point A and an ending point B. The direction of the vector AB may then be used to move desired components along the vector AB, and the length of the vector AB may provide for the length of the movement. Pinch-to-zoom gestures 392 may also be used. For example, spreading two fingers outwardly along a line 394 may zoom certain portions of the screen 240. Likewise moving two fingers inwardly along a line 396 may unzoom certain portions of the screen 240.

Rotational gestures 398 may also be provided. For example, rotating one or two fingers to follow arcs 400 and 403 may correlatively rotate desired components of the NDT device 12. Multi-gesture control 404 is also provided. For example, using three fingers or more and swiping in directions 406, 408 may shift the screen 240 to display an entirely new screen, such as a screen containing a different set of virtual controls or a different software application. Force feedback gestures 410 or techniques may additionally be used. For example, pressing a finger with a force 412 may result in a movement of a desired component correlative to the force 412. The stronger the force 412, the faster the movement. Likewise, the force 412 may be used, such as when tapping on the screen 240, to provide for jogging or fine control of desired components.

Figure 13:
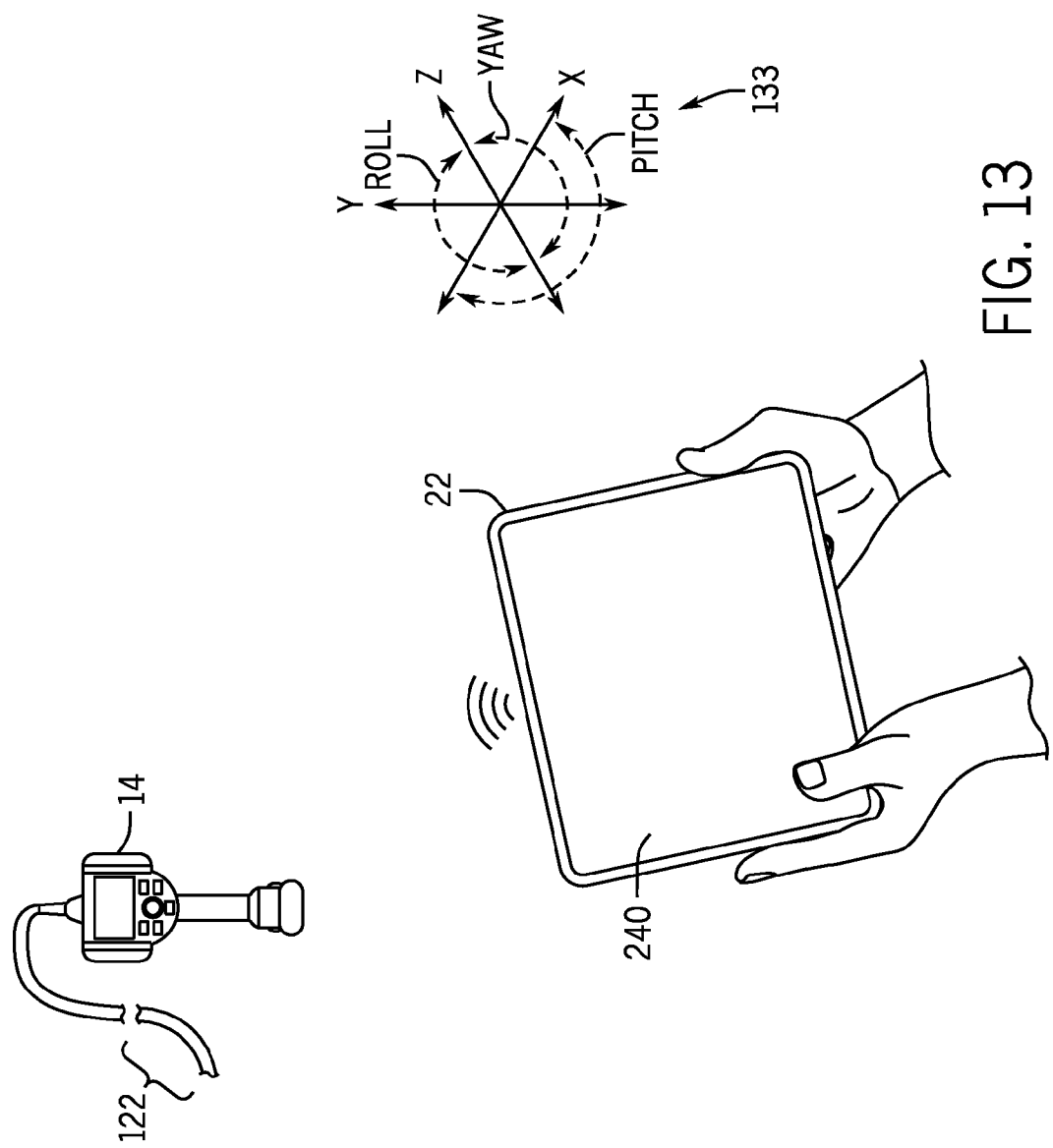
FIG. 13 is a perspective view on an embodiment of the mobile device of FIG. 1 suitable for motion and/or voice control.

In certain embodiments, the mobile device 22 may include accelerometers, gyroscopes, and other sensors useful in deriving motion and/or orientation of the mobile device 22. Accordingly, as depicted in FIG. 13, moving and/or changing orientations of the mobile device 22 may be used to control features of the NDT devices 12, such as the articulating section 122 of the borescope 14. Indeed, by virtually "driving" the mobile device 22 it may be possible to remotely control the NDT devices 12. Six degrees of freedom of movement may be derived with respect to the axes 133, such as movements perpendicular to the X, Y, Z axes 133 (e.g., translation in the axes 133), rotations about the X, Y, Z axes 133, and/or rotative movements with respect to each of the axes 133 (e.g., pitch, yaw, roll). The movements may be derived and subsequently mapped to correlative movements of the NDT devices 12, such as movements of the articulating section 122 of the borescope 14, and pan/tilt/zoom movements of the PTZ camera 16. By providing for the virtual driving of the mobile device 22, it may be possible to further maximize screen 240 space, for example, by not including the joystick 232 and the control pad 234.

Voice commands may be provided, additional or alternative to the aforementioned virtual controls. For example, voice may be processed by the NDT devices 12, by the mobile device 22, by the cloud 24, by devices coupled to the cloud 24 (e.g., device 29), or by a combination thereof, to parse voice into useful commands. All aspects of the NDT devices 12 may be controlled using voice, including positioning components of the NDT devices 12 (e.g., articulating section 122 of the borescope 12), recording images and video, providing for annotations, controlling parameters as described above, and so on.

It should be noted that the patent application U.S. Pat. No. 6,830,545 entitled, "Tube Gripper Integral with Controller for Endoscope of Borescope" that was filed on May 13, 2002 is hereby incorporated by reference. The incorporated application relates generally to a tube gripper with a channel to receive a probe insertion tube, and a controller input to control a function of the probe.

Figure 14:
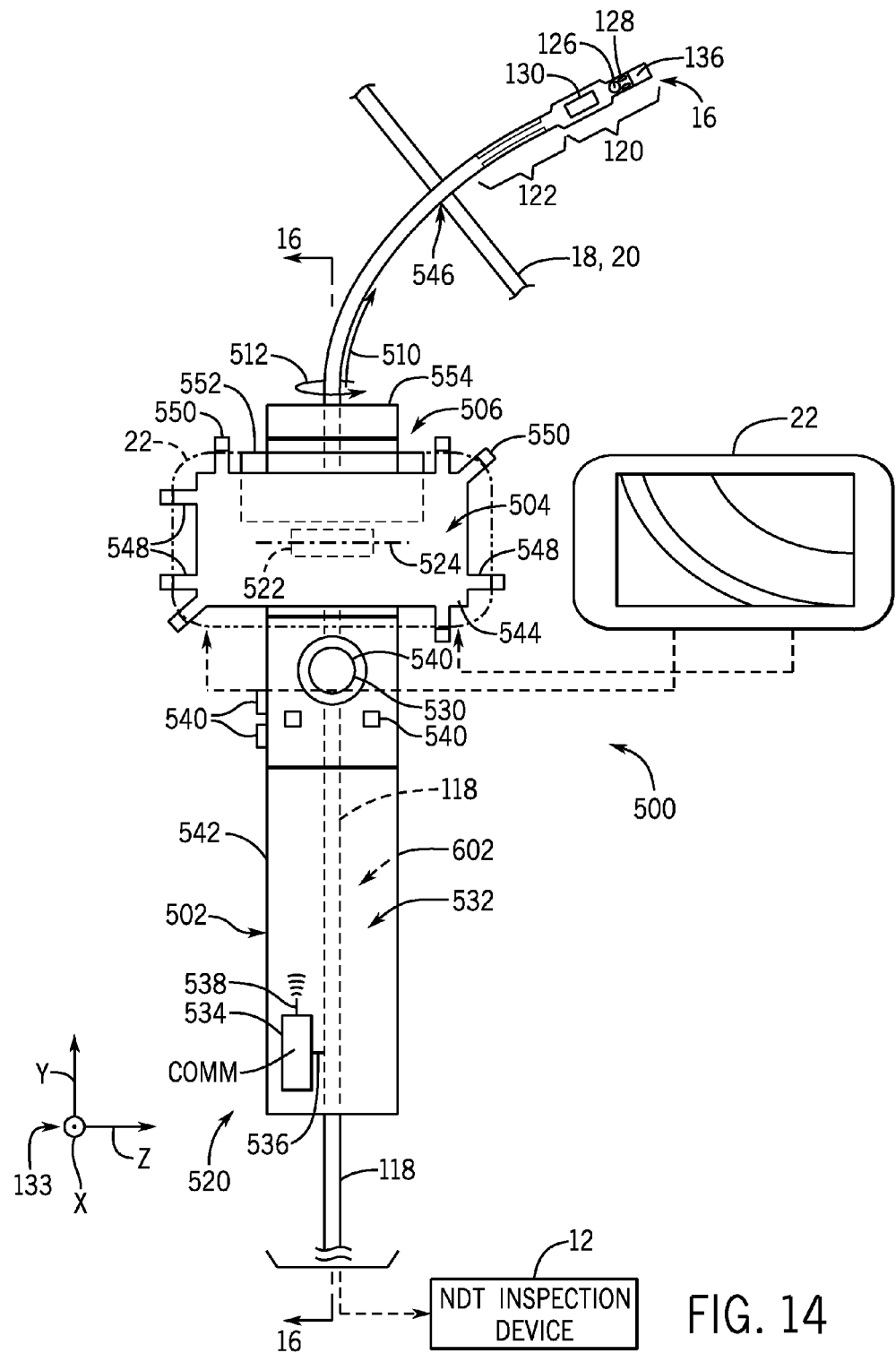
FIG. 14 is a top view of an embodiment of a mobile handset, in accordance with an embodiment.

Returning to the drawings, FIG. 14 is an embodiment of a mobile handset 500 that enables the sensors 126 (e.g., borescope camera, vibration sensor, X-ray sensor, eddy current sensor, ultrasonic sensor, temperature sensor, pressure sensor, position sensor) of the NDT inspection device 12 to be controlled, monitored, and/or viewed separate from the NDT inspection device 12. As discussed above, the NDT inspection device 12 may be a borescope 14, an eddy current inspection device 92, an ultrasonic inspection device 94, or a digital radiography device 96. While a PTZ camera 16 is shown on the head end section 120 of FIG. 14, the mobile handset 500 may be utilized with NDT inspection devices 12 having other sensors 126 on the head end section 120. The mobile handset 500 includes a handle portion 502, a cradle portion 504, and a gripper portion 506. The mobile handset 500 and attached mobile device 22 may be smaller and/or lighter than the NDT inspection device 12. The handle portion 502 may be shaped to accommodate a hand of an operator. The insertion tube 118 passes through at least some of the handle portion 502. The gripper portion 506 grips the insertion tube 118 to secure the mobile handset 500 to the insertion tube 118. The gripper portion 506 fixes the movement of the mobile handset 500 in an axial direction 510 and a tangential direction 512 to corresponding movements of the insertion tube 118. That is, engaging the gripper portion 506 enables an operator to insert, remove, and rotate the insertion tube 118 by corresponding movements of the gripper portion 506.

Figure 15:
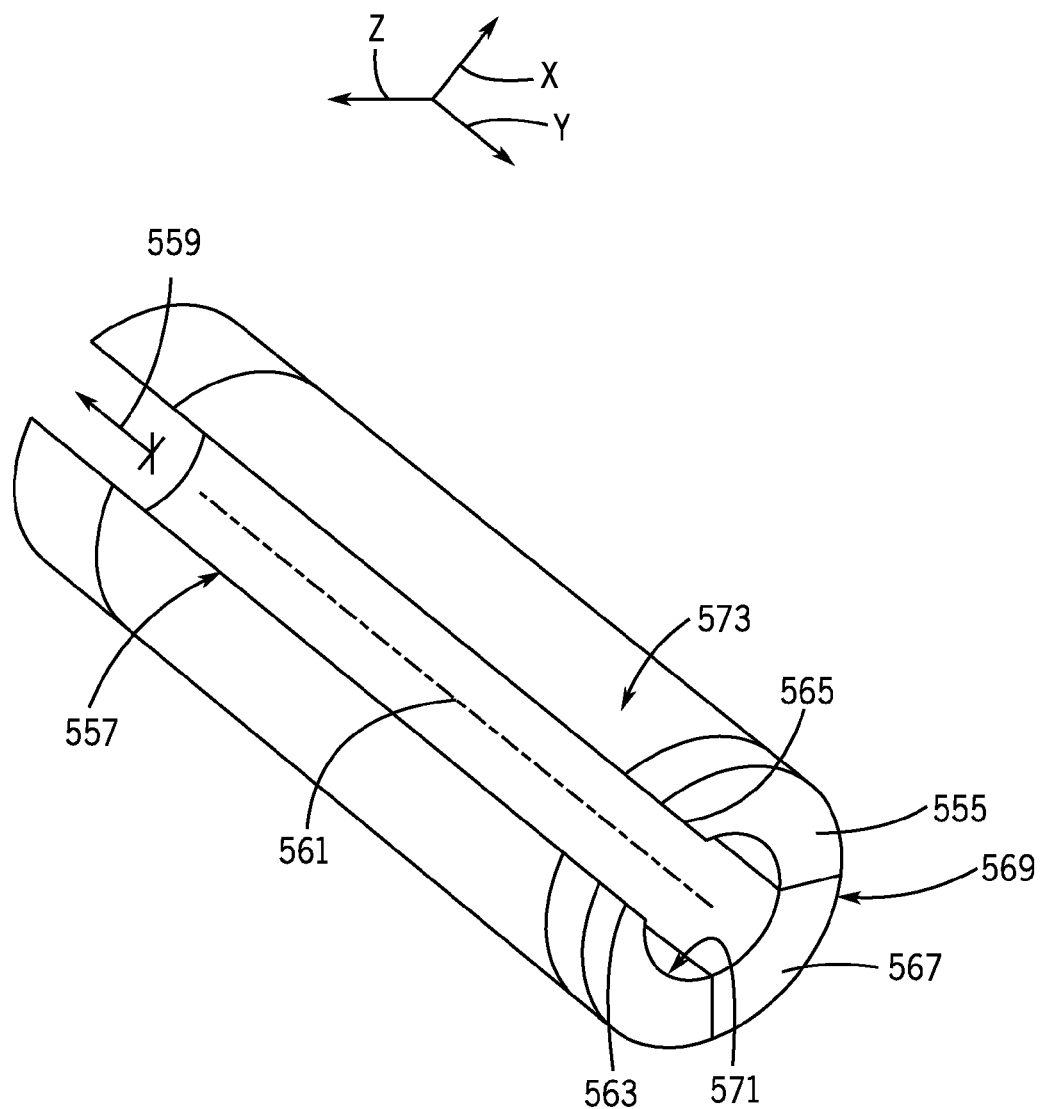
FIG. 15 is a perspective view of an embodiment of a gripper of the mobile handset of FIG. 14.
Figure 16:
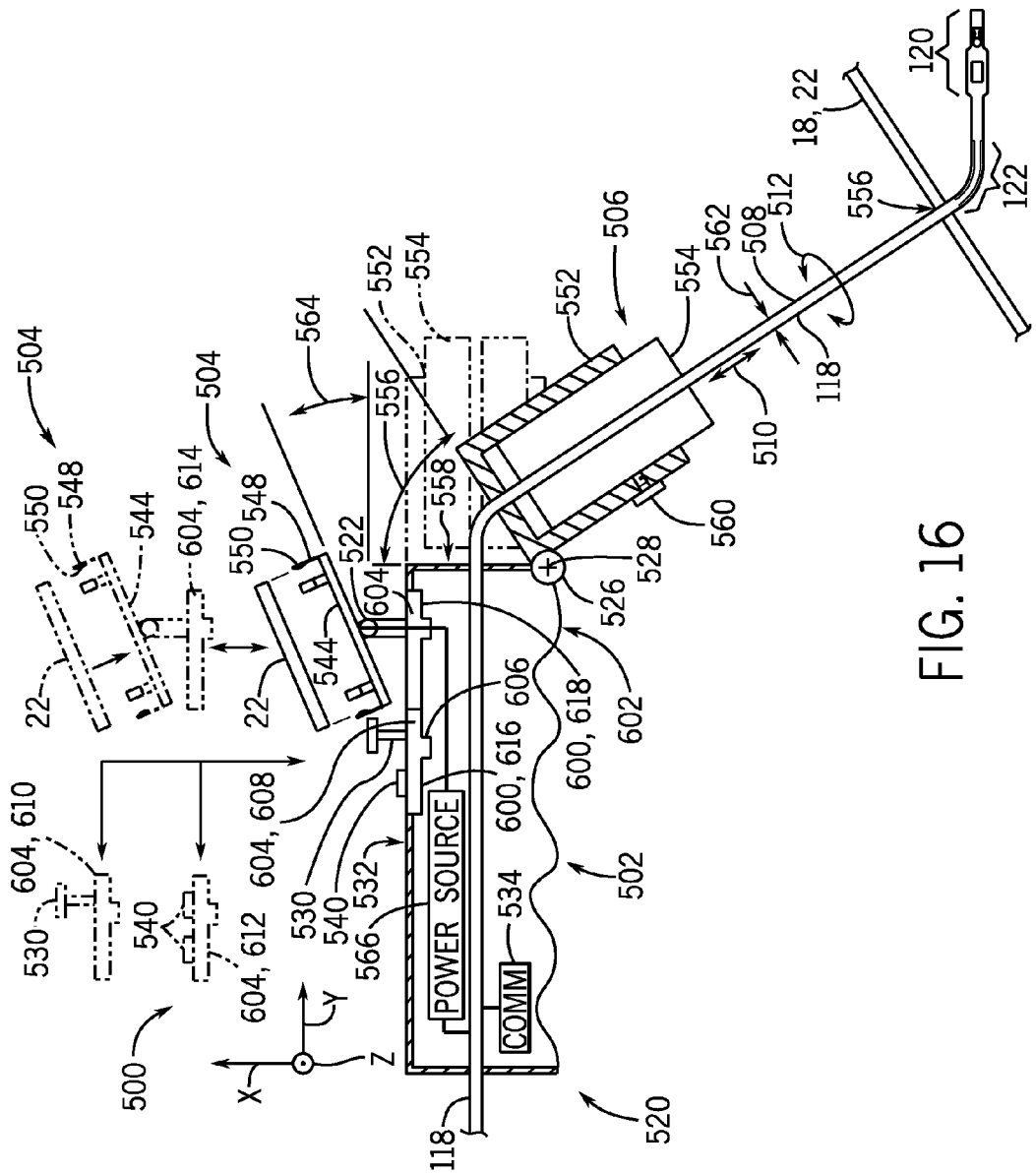
FIG. 16 is a cross-sectional view of an embodiment of the mobile handset of FIG. 14, taken along line 16-16.

For ease of explanation, the mobile handset 500 is described in relation to a coordinate system with the X, Y, and Z axes 133. Points higher along the X-axis are referred to as "above," "over," and so forth, whereas points lower along the X-axis are referred to as "below," "under," and so forth. Points along the Y-axis extend substantially through the mobile handset 500. Motion along the Y-axis is referred to as longitudinal motion or motion in a longitudinal direction. The Y-axis is defined herein for FIGS. 14-17 as relative to the mobile handset 500. The Z-axis extends through a handset end portion 520 of the mobile handset 500. In some embodiments, the cradle portion 504 and/or the gripper portion 506 move relative to the handle portion 502. For example, the cradle portion 504 is joined to the handle portion 502 by a first joint 522 (e.g., hinge) to enable the cradle portion 504 to rotate about a first axis 524. As shown in FIG. 16, the gripper portion 506 is joined to the handle portion 502 by a second joint 526 to enable the gripper portion 506 to rotate about a second axis 528. The cradle portion 504 and the gripper portion 506 are joined to the handle portion 502 by any of a variety of joints, including but not limited to hinges, slider joints, spherical joints, or any combination thereof. In this way, the cradle portion 504 and/or the gripper portion 506 are adjustable to accommodate a preference of an operator regarding how the mobile handset 500 is positioned relative to the insertion tube 118.

In some embodiments, as shown in FIG. 14, the handle portion 502 includes a handset joystick 530 to control the NDT inspection device 12. For example, the handset joystick 530 may control the position and orientation of the head end section 120, control a cursor or indicator on the mobile device 22, perform a measurement, annotate images from the PTZ camera 16, and so forth. The handset joystick 530 is positioned on a top surface 532 of the handle portion 502 to readily accommodate manipulation with a thumb of the operator. In some embodiments, the handset joystick 530 controls the articulation section 122 to adjust the position and/or orientation of the sensors 126 of the head end section 120. Control signals from the handset joystick 530 to adjust the articulating section 122 may be transmitted to the NDT inspection device 12 via a communications interface 534 within the mobile handset 500 and/or via the mobile device 22 removably attached to the cradle portion 504.

In some embodiments, the handset joystick 530 enables the operator to control operations on the mobile device 22 without direct input to the mobile device 22, such as via a touchscreen. The mobile device 22 attached to the cradle portion 504 is an output device to provide output signals to the operator (e.g., audio signals, visual signals). In some embodiments, the mobile device 22 (e.g., touch screen) is an input and output device that enables the operator to provide input signals to the NDT inspection device 12, or to manipulate output information displayed on the mobile device 22. In some embodiments, the communications interface 534 communicates with the NDT inspection device 12 via a wired or wireless connection. For example, a data connection 536 may communicatively couple the communications interface 534 of the mobile handset 500 to the NDT inspection device 12 via the insertion tube 118. The communications interface 534 may include an antenna 538 to communicate wirelessly with the NDT inspection device 12. The insertion tube 118 transmits data between the sensors 126 in the head end section 120 to the NDT inspection device 12. In some embodiments, the communications interface 534 communicates via a wired or wireless connection with the mobile device 22. That is, the mobile handset 500 may be an intermediary communications hub for the mobile device 22 and the NDT communications device 12.

In some embodiments, the mobile device 22 communicates information (e.g., control signals, receive image data or sensor data) directly with the NDT inspection device 12 rather than transmitting the information through the communications interface 534 and the insertion tube 118. As discussed above, the mobile device 22 may include a GUI to view sensor data from the sensors 126 and to control or manipulate the articulating section 122. The communications interface 534 and/or the mobile device 22 may communicate with NDT inspection device 12 using any of a plurality of communications standards, protocols and technologies, including but not limited to Global System for Mobile Communications (GSM), Enhanced Data GSM Environment (EDGE), high-speed downlink packet access (HSDPA), wideband code division multiple access (W-CDMA), code division multiple access (CDMA), time division multiple access (TDMA), Bluetooth, Wireless Fidelity (Wi-Fi) (e.g., IEEE 802.11a, IEEE 802.11b, IEEE 802.11g and/or IEEE 802.11n), Wi-MAX, and/or Short Message Service (SMS), or any other suitable communication protocol, including communication protocols not yet developed as of the filing date of this document.

In some embodiments, the handle portion 502 includes one or more operator inputs 540 to select, analyze, process, or otherwise manipulate sensor data on the mobile device 22 that is received from the sensors 126 of the head end section 120. Operator inputs 540 may be positioned on the top surface 532, a side surface 542, or a bottom surface 602. Operator inputs 540 (e.g., user interface devices) may include one or more buttons, a trigger, or the handset joystick 530. Operator inputs 540 on the top surface 532 are positioned to enable a thumb of the operator to manipulate the sensor data on the mobile device 22. For example, the handset joystick 530 is an operator input 540 that enables the operator to move the head end section 120 and sensors 126, to control the NDT inspection device 12, and/or to manipulate the sensor data on the mobile device 22. Operator inputs 540 on the side surface 542 or bottom surface 602 are positioned to enable a finger or thumb of the operator to manipulate the sensor data on the mobile device 22. The operator inputs 540 may be arranged on any surface of the mobile handset 500 to provide the operator with convenient control of the mobile device 22 and/or the head end section 120. The mobile handset 500 communicates signals from the operator inputs 540 with the NDT inspection device 12 via the communications interface 534 and/or the mobile device 22.

Embodiments arrange the mobile handset 500 downstream of the NDT inspection device 12 and upstream of the sensors 126 and head end section 120. That is, the mobile handset 500 and mobile device 22 are arranged between an inspection point 546 and the NDT inspection device 12. The NDT inspection device 12 controls the head end section 120 and monitors the sensors 126 based at least in part on control signals received from the mobile handset 500 or mobile device 22 (e.g., control signals from the handset joystick 530, operator inputs 540, and/or the GUI of the mobile device 22). Accordingly, an operator with the mobile handset 500 may control the head end section 120 at a position downstream from the NDT inspection device 12. In some embodiments, the mobile handset 500 may be positioned near the inspection point 546 of the turbomachinery 18 or the site 20, whereas the NDT inspection device 12 is positioned a further distance from the inspection point 546. The handset joystick 530, operator inputs 540, and/or the GUI of the mobile device 22 enable the operator to control the head end section 120 and/or to monitor the sensors 126 without the operator moving to the NDT inspection device 12 to directly input controls for the head end section 120.

The cradle portion 504 includes a mounting plate 544 that removably mounts with the mobile device 22. As discussed above, the mobile device 22 may be a portable phone (e.g., smart phone), a tablet, a media player, a personal data organizer, a global positioning system receiver, or any combination of such devices. In some embodiments, the mounting plate 544 includes a plurality of arms 548 that receive the mobile device 22. The mounting plate 544 supports and retains the mobile device 22 along the X-axis, and the plurality of arms 548 support and retain the mobile device 22 along the Y-axis and the Z-axis. Some of the arms 548 include a retaining feature 550 (e.g., rubber end) that retains the mobile device 22 within the cradle portion 504 by an interference or friction fit. That is, the retaining features 550 are molded around edges of the mobile device 22 to retain the mobile device 22 in the cradle portion 504. By way of example, the mounting plate 544 may be a model of an iPhone Cradle available from Zacuto of Chicago, Ill.

The arms 548 of the cradle portion 504 at least partially enclose an edge of the mobile device 22 to mount the mobile device 22. In some embodiments, the mobile device 22 is inserted (e.g., snapped, docked) into the cradle portion 504. The mobile device 22 may be removably mounted to the cradle portion 504 by a snap fastener, a suction fastener, a magnetic fastener, a threaded fastener, and so forth. In some embodiments, the cradle portion 504 is adjustable to accommodate multiple mobile device geometries. The capability to removably mount with a variety of mobile devices 22 may increase the versatility of the mobile handset 500 for operators. In some embodiments, the data processing and storage capabilities of the mobile device 22 are accessible by the mobile handset 500, expanding the data processing and storage capabilities of the mobile handset 500 and/or the NDT inspection device 12. For example, image data may be stored within the removable mobile device 22 for later analysis by the operator without a separate step to transfer image data to the operator. Various mobile devices 22 attached to the mobile handset 500 by the operator may provide additional functionalities to the mobile handset 500. For example, a portable phone secured by the mobile handset 500 may enable the operator to make a telephone call or to readily share image data over a network while using the mobile handset 500. Moreover, the operator may use a first mobile device 22 (e.g., smart phone) while operating alone, and a larger second mobile device 22 (e.g., tablet computer) while operating with others, such as for instructional, demonstration, or consulting use.

The gripper portion 506 of the embodiment of FIG. 14 is joined to the handle portion 502 below the cradle portion 504. The gripper portion 506 includes a receiver 552 and a barrel 554. The barrel 554 engages the insertion tube 118 to secure the barrel 554 to the insertion tube 118. The barrel 554 may be shaped to accommodate different insertion tube geometries (e.g., large or small diameter 562, circular shape, square shape, and so forth). The barrel 554 engages the insertion tube 118 to fix the movement of the insertion tube 118 in the axial direction 510 and the tangential direction 512 to corresponding movements of the barrel 554. The outer surface of the barrel 554 provides a larger surface to manually insert, remove, and rotate the insertion tube 118 relative to the inspection point 546 compared to the surface of the insertion tube 118 alone. The receiver 552 engages the barrel 554 to join the mobile handset 500 to the insertion tube 118. For example, the receiver 552 may substantially surround and secure the barrel 554 in the axial direction 510.

In some embodiments, the barrel 554 engages the insertion tube 118 separate from the mobile handset 500. That is, an operator may engage the barrel 554 about the insertion tube 118 and utilize the mobile device 22 without utilizing the mobile handset 500. In some embodiments, the barrel 554 is twisted along the Y-axis to engage the insertion tube 118, such as by a ratchet and/or a threaded connection. The barrel 554 may be annular or C-shaped. FIG. 15 illustrates a perspective view of a C-shaped barrel 555. A C-shaped barrel 555 has an opening 557 along a side in a radial direction 559 from an axis 561. The opening 557 enables the C-shaped barrel 555 to engage the insertion tube 118 without removing the head end 120 from the inspection point 546. That is, the C-shaped barrel 555 may attach to the insertion tube 118 without moving the insertion tube 118 along the axis 561 (e.g., the Y-axis). In some embodiments, the C-shaped barrel 555 engages the insertion tube 118 when a first opening end 563 is guided toward a second opening end 565 across the opening 557. In some embodiments, a flexible portion 567 of the C-shaped barrel 555 enables the opening 557 to expand or contract to accommodate various diameters 562 of the insertion tube 118. The flexible portion 567 may include, but is not limited to, an elastomer, a metal, or a plastic, or any combination thereof. The first opening end 563 and the second opening end 565 may be formed of the same or different material as the flexible portion 567. The operator may grasp an outer surface 569 to engage an inner surface 571 with the insertion tube 118. The outer surface 569 may have a textured (e.g., knurled) surface 573 to aid manual manipulation of the C-shaped barrel 555 and the insertion tube 118. In some embodiments, the C-shaped barrel 555 may be inserted into the receiver 552 of the mobile handset 500. The receiver 552 interfaces with the outer surface 569 to guide the first opening end 563 toward the second opening end 565, thereby engaging the inner surface 571 with the insertion tube 118.

FIG. 16 is a cross-sectional view of the mobile handset 500 of FIG. 14 along line 8-8. The handle portion 502 has molded shape to substantially conform to the hand of the operator. The gripper portion 506 joins at the second joint 526 on the handle portion 502 to enable the gripper portion 506 to adjust through a range of motion 556 about the second axis 528 relative to the handle portion 502. A mounting end portion 558 of the handle portion 502 enables the insertion tube 118 to flex to accommodate the range of motion 556. For example, the mounting end portion 558 may be shaped so that the insertion tube 118 flexes gradually through the handle portion 502 and the gripper portion 506 rather than sharply at the mounting end portion 558. The shape of the mounting end portion may increase the usable life of the insertion tube 118. The gripper portion 506 and the cradle portion 504 are mounted to the handle portion 502 at the mounting end portion 558. Rotating the gripper portion 506 about the second joint 526 may increase the operational flexibility of the mobile handset 500 and enables the operator to adjust the position of the mobile device 22. For example, the handle portion 502 and the cradle portion 504 may be positioned so that one or more operators may readily observe the images of the mobile device 22, while the gripper portion 506 is rotated about the second joint 526 so that the sensors 126 in the head end section 120 is properly positioned without affecting the orientation of the handle portion 502.

In some embodiments, the barrel 554 is removably attached to the receiver 552. For example, a barrel fastener 560 secures the barrel 554 to the receiver. In other embodiments, the barrel 554 may be integrally formed with the receiver 552 or attached to the receiver 552 by a threaded connection, snap fit, or friction fit. The barrel 554 and/or the receiver 552 may be modular components, such that various barrels 554 and receivers 552 may be joined to the handle portion 502 to accommodate insertion tubes 118 with various diameters. For example, a diameter 562 of the insertion tube 118 may be between approximately 3 to 10 mm (0.12 to 0.39 in), approximately 5 to 8 mm (0.2 to 0.31 in), or approximately 6 to 7 mm (0.24 to 0.28 in). By way of example, the insertion tube 118 and head end section 120 may be a model of a QuickChange™ Probe available from General Electric, Skaneateles, N.Y.

As discussed above, the cradle portion 504 is attached to a first joint 522 to enable the cradle portion 504 to move relative to the handle portion 502 as shown by arrow 564. The operator may adjust the position of the cradle portion 504 to improve the visibility of the mobile device 22. In some embodiments, the handle portion 502 includes a power source 566. Embodiments of the power source 566 include one or more batteries (e.g., lithium-ion, lithium-polymer, alkaline, and so forth) or a power converter to convert power supplied by an external source (e.g., NDT inspection device 12). The power source 566 may supply sufficient power for the communications interface 534 to communicate with the NDT inspection device 12 and/or the mobile device 22. The power source 566 may also supply power to the communications interface 534. In some embodiments, the power source 566 may supply power to the mobile device 22 via a wired or wireless connection. For example, the mounting plate 544 may have a coil to supply power inductively to the mobile device 22. Alternatively, the mounting plate 544 may supply power to the mobile device 22 via a wired connection.

In some embodiments, one or more user interface devices (e.g., operator inputs 540, mobile device 22, cradle portion 504) may be removably docked to the handle portion 502. The handle portion 502 may include one or more docks 600 on the top surface 532, the side surfaces 542, or a bottom surface 602, or any combination thereof. Some components, such as the cradle portion 504 and operator inputs 540, may be removably docked via a module 604 (e.g., mounting plate, plug). The module 604 may be removably coupled to the dock 600 by a physical connection 606 (e.g., plug, snap, fastener, friction fit) or magnetic connection. The mobile device 22 or the operator inputs 540 may interface with the power source 566 or communications interface 534 via a wired or wireless connection between the dock 600 and the module 604. The modules 604 with the user interface devices are removable, thereby enabling the layout of input controls and output display of the NDT inspection device 12 to be customized by the operator. For example, the operator may remove a first user interface device 608 having the operator input 540 and the handset joystick 530, and replace the first user interface device 608 with a second user interface device 610 having only the handset joystick 530, or with a third user interface device 612 having multiple operator inputs 540.

In some embodiments, a user interface device may be docked in different docks 600 based at least in part on a preference of the operator. For example, a cradle user interface device 614 may be removably docked in a first dock 616 when utilizing the virtual joystick on the mobile device 22, and the cradle user interface device 614 may be removably docked in a second dock 618 when utilizing the handset joystick 530 of an input module 604 removably docked in the first dock 616. In some embodiments, the mobile device 22 may communicate wirelessly with the communications interface 534, or communicate wirelessly with the NDT inspection device 12 regardless of whether the cradle user interface device 614 is docked with the handle portion 502. Docking the cradle user interface device 614 in a dock 600 when a mobile device 22 is in the cradle portion 504 may enable (e.g., synchronize) the mobile device 22 to display output of the NDT inspection device 12, and/or to control functions of the NDT inspection device 12. Various cradle user interface devices 614 with different cradle portions 504 may be utilized to enable mobile devices 22 with different geometries to be utilized with the mobile handset 500.

Figure 17:
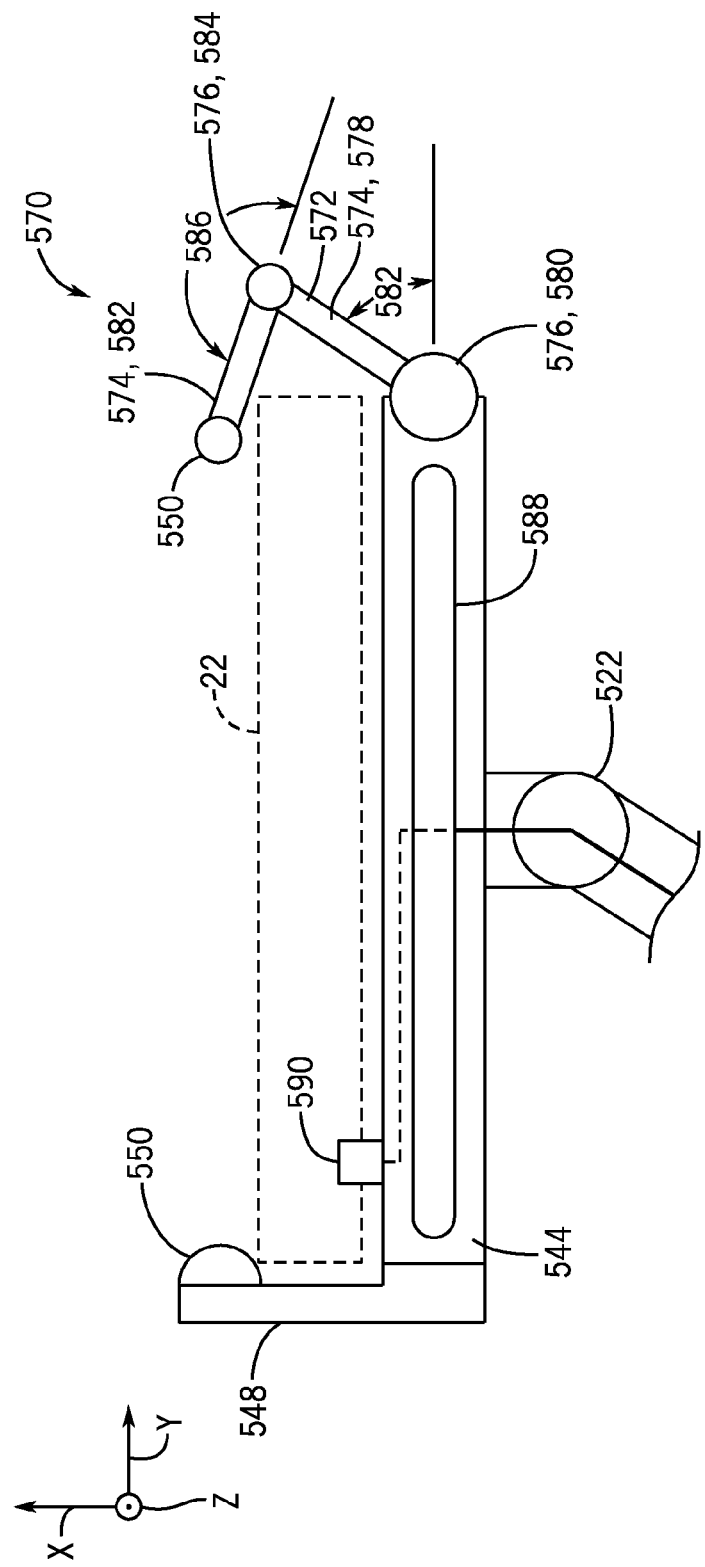
FIG. 17 is a side-view of an embodiment of a cradle portion of the mobile handset.

An adjustable cradle portion 570 may accommodate mobile devices 22 with different geometries, which may increase the modularity and utility of the mobile handset 500. For example, operators with different mobile devices 22 may utilize the same mobile handset 500. FIG. 17 is a cross-sectional view of an embodiment of the adjustable cradle portion 570. In the present embodiment, an adjustable arm 572 wraps around a portion of the mobile device 22 to secure the mobile device 22 within the adjustable cradle portion 570. The adjustable arm 572 includes at least one member 574 and at least one adjustable joint 576. Increasing the number of members 574 and adjustable joints 576 may increase the flexibility of the adjustable arm 572. The adjustable arm 572 enables the cradle portion 504 to removably secure mobile devices 22 of various geometries. The ability to removably attach the adjustable cradle portion 570 with mobile devices 22 of various geometries may increase the versatility of the mobile handset 500. For example, a first operator may removably attach a portable phone to the cradle portion 504 to view the sensor data from the sensors 126 in the head end section 120 and/or to control the articulating section 122. The first operator may remove the portable phone to make a phone call regarding observations from the sensors 126, and a second operator may attach a different mobile device 22 (e.g., a tablet computer) having a different geometry from the portable phone to the cradle portion 504 to continue monitoring the sensor data from the sensors 126 and/or to continue controlling the articulating section 122.

In some embodiments, the first member 578 rotates about the first adjustable joint 580 as shown by the arrow 582. As shown, the first member 578 adjusts to accommodate mobile devices 22 with varying lengths along the Y-axis. The second member 582 rotates about the second adjustable joint 584 as shown by the arrow 586 to secure the mobile device 22. As shown, the second member 582 adjusts to accommodate mobile devices 22 with varying depths along the X-axis. In some embodiments, the mounting plate 544 has multiple adjustable arms 572 to secure the mobile device 22 within the adjustable cradle portion 570

In some embodiments, a coil 588 within the mounting plate 544 supplies power inductively to the mobile device 22. The coil 588 charges a battery of the mobile device 22 and/or supplies power for the mobile device 22 to operate. The coil 588 is arranged in the mounting plate 544 or in the handle portion 502. In some embodiments, a plug 590 connects with the mobile device 22 to supply power to the mobile device 22 and/or to transfer signals between the mobile device 22 and the communications interface 534.

Technical effects of the invention include enabling a mobile device 22 to be mounted in a cradle portion 504 of a mobile handset 500 between sensors 126 in the head end section 120 and an NDT inspection device 12. The mobile handset 500 may accommodate various geometries of mobile devices 22. The mobile device 22 is placed in a readily viewable position and/or orientation relative to the mobile handset 500 while the operator manually controls the insertion tube 118. Mounting the mobile device 22 in the mobile handset 500 enables the mobile device operator to manually control (e.g., insert) the insertion tube 118 while using the mobile device 22 to monitor and/or to control the head end section 120. The mobile handset 500 may include a handset joystick 530 and operator inputs 540 to control the articulating section 122, sensors 126, or to manipulate sensor data via the mobile device 22. The cradle portion 504 and/or the operator inputs 540 may be removably docked with the mobile handset 500. These removable components enable the operator to customize which components to dock with the mobile handset 500, and where to dock the components on the mobile handset 500. A communications interface 534 of the mobile handset 500 may communicatively couple with the mobile device 22 and/or the NDT inspection device 12. The communications interface 534 enables the mobile handset 500 to transmit signals with the NDT inspection device 12 to monitor and/or to control the head end section 120. Further, the mobile handset 500 may provide power to the mobile device 22, and/or directly connect the mobile device 22 to the NDT inspection device 12.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

The invention claimed is:
1. A mobile handset, comprising:
   a handle portion comprising a first dock configured to removably receive a user interface device;
   a gripper portion coupled to the handle portion, wherein the gripper portion is configured to receive an insertion tube of a non-destructive testing (NDT) inspection device through the gripper portion, to control a position and an orientation of the insertion tube relative to an inspection point when the gripper portion is engaged with the insertion tube, and to enable the insertion tube to move in an axial direction through the gripper portion when the gripper portion is not engaged with the insertion tube; and the user interface device removably coupled to the first dock, wherein the user interface device is configured to control the NDT inspection device.

2. The handset of claim 1, wherein the first dock comprises a cradle portion configured to receive a mobile device, and the mobile device comprises the user interface device.

3. The handset of claim 2, wherein the cradle portion is configured to removably couple with the mobile device by at least one of a friction fit, a snap fastener, a suction fastener, a magnetic fastener, or a threaded fastener, or any combination thereof.

4. The handset of claim 2, wherein the cradle portion is adjustable to accommodate multiple mobile device geometries.

5. The handset of claim 1, wherein the user interface device comprises a handset joystick, one or more buttons, a trigger, or any combination thereof, and the user interface device is configured to control an articulating section of the insertion tube.

6. The handset of claim 1, wherein the user interface device comprises a mobile device, and the mobile device is configured to control an articulating section of the insertion tube.

7. The handset of claim 1, comprising the NDT inspection device, wherein the NDT inspection device comprises a borescope, an eddy current inspection device, an ultrasonic inspection device, or an x-ray inspection device, or any combination thereof.

8. The system of claim 7, wherein the NDT inspection device comprises an articulating section configured to be inserted into the inspection point, wherein the user interface device is configured to control movement of the articulating section.

9. A mobile handset, comprising
a first dock configured to removably receive a mobile device, and the mobile device is communicatively coupled to a non-destructive testing (NDT) inspection device;
a gripper portion coupled to the first dock, wherein the gripper portion is configured to receive an insertion tube of the NDT inspection device through the gripper portion, the gripper portion is configured to engage with the insertion tube to control a position and an orientation of the insertion tube relative to an inspection point and the gripper portion is configured to move in an axial direction to a plurality of axial positions about the insertion tube when the gripper portion is not engaged with the insertion tube; and
a communications interface communicatively coupled to the NDT inspection device, wherein the communication interface is configured to communicate signals to the NDT inspection device to control an articulating section of the insertion tube, wherein the articulating section of the insertion tube is configured to be inserted into the inspection point.

10. The handset of claim 9, wherein the mobile handset comprises a power source configured to supply power to the mobile device.

11. The handset of claim 9, comprising a handle portion, wherein at least one of the cradle portion and the gripper portion is rotatably coupled to the handle portion via a joint.

12. The handset of claim 9, wherein the mobile device is configured to control the articulating section of the insertion tube of the NDT inspection device via the communications interface.

13. The handset of claim 9, comprising a second dock configured to removably receive a user interface device, wherein the user interface device comprises a handset joystick, one or more buttons, a trigger, a touch screen, or any combination thereof.

14. A system, comprising:
a borescope, comprising:
a camera configured to transmit image signals along an insertion tube;
storage circuitry capable of storing one or more executable routines, image signals, or both; and
processing circuitry configured to execute one or more executable routines, to control the camera, to process image signals into image data, and to transmit the image data to a user interface device; and
a mobile handset coupled to the insertion tube, wherein the mobile handset comprises:
a handle portion comprising a first dock configured to removably receive the user interface device, wherein the user interface device is configured to communicate with the processing circuitry; and
a gripper portion coupled to the handle portion, wherein the gripper portion is configured to receive the insertion tube through the gripper portion, and the gripper portion is configured to engage the insertion tube at a plurality of different axial positions to control a position of the mobile handset relative to the camera of the insertion tube.

15. The system of claim 14, wherein the first dock comprises a cradle portion configured to receive a mobile device, wherein the mobile device comprises the user interface device and the mobile device is configured to control the borescope.

16. The system of claim 14, wherein the first dock is adjustable relative to the handle portion, relative to the gripper portion, or any combination thereof.

17. The system of claim 14, wherein the user interface device is configured to display the image data.

18. The system of claim 14, wherein the mobile handset comprises a power source.

19. The system of claim 14, comprising the user interface device removably coupled to the first dock, wherein the user interface device is configured to control the borescope.

20. The system of claim 14, wherein the gripper portion is configured to accommodate at least two insertion tube geometries.

* * * * *